US009499808B2

(12) United States Patent
Harris et al.

(10) Patent No.: US 9,499,808 B2
(45) Date of Patent: Nov. 22, 2016

(54) USING CYTOSINE DEAMINASES TO DIMINISH RETROELEMENT TRANSFER FROM PIGS TO HUMANS

(75) Inventors: Reuben S. Harris, St. Paul, MN (US); Stefan R. Jonsson, Kopavogur (IS); Scott C. Fahrenkrug, Minneapolis, MN (US); Rebecca St. Claire Larue, Lauderdale, MN (US)

(73) Assignee: Recombinetics, Inc., Saint Paul, MN (US)

( * ) Notice: Subject to any disclaimer, the term of this patent is extended or adjusted under 35 U.S.C. 154(b) by 1746 days.

(21) Appl. No.: 12/622,886

(22) Filed: Nov. 20, 2009

(65) Prior Publication Data
US 2010/0251395 A1  Sep. 30, 2010

Related U.S. Application Data

(63) Continuation of application No. 12/243,711, filed on Oct. 1, 2008, now abandoned, which is a continuation of application No. 11/472,743, filed on Jun. 22, 2006, now abandoned.

(60) Provisional application No. 60/694,054, filed on Jun. 24, 2005.

(51) Int. Cl.
 C12N 9/78 (2006.01)
 A01K 67/027 (2006.01)
 C12N 15/85 (2006.01)

(52) U.S. Cl.
 CPC ............ *C12N 9/78* (2013.01); *A01K 67/0273* (2013.01); *A01K 67/0275* (2013.01); *C12N 15/8509* (2013.01); *A01K 2207/15* (2013.01); *A01K 2217/00* (2013.01); *A01K 2217/05* (2013.01); *A01K 2217/075* (2013.01); *A01K 2227/108* (2013.01); *A01K 2267/02* (2013.01); *A01K 2267/025* (2013.01); *A01K 2267/0337* (2013.01); *C12N 2517/02* (2013.01); *C12N 2740/13011* (2013.01)

(58) Field of Classification Search
 CPC ..................... A01K 2227/108; A01K 2267/00; A01K 2267/025; C12N 9/78; C12N 15/8509; C12N 2517/02
 USPC ........................................... 435/325; 800/17
 See application file for complete search history.

(56) References Cited

U.S. PATENT DOCUMENTS

| 4,873,191 A | 10/1989 | Wagner et al. |
| 5,139,941 A | 8/1992 | Muzyczka et al. |
| 5,610,053 A | 3/1997 | Chung et al. |
| 5,731,178 A | 3/1998 | Sippel et al. |
| 6,100,448 A | 8/2000 | Thompson et al. |
| 6,395,549 B1 | 5/2002 | Tuan et al. |
| 6,548,741 B2 | 4/2003 | DeSousa et al. |
| 6,613,752 B2 | 9/2003 | Kay et al. |
| 6,700,037 B2 | 3/2004 | Damiani et al. |
| 2004/0009951 A1* | 1/2004 | Malim et al. ................... 514/44 |
| 2004/0203158 A1* | 10/2004 | Hackett et al. ............... 435/473 |
| 2005/0003542 A1 | 1/2005 | Kay et al. |
| 2005/0266561 A1* | 12/2005 | Wells ........................... 435/455 |
| 2006/0019262 A1 | 1/2006 | Petersen-Mahrt et al. |
| 2006/0024280 A1 | 2/2006 | West |
| 2006/0148080 A1 | 7/2006 | Diamond |
| 2007/0134212 A1 | 6/2007 | Beschorner et al. |

FOREIGN PATENT DOCUMENTS

WO  03/095636 A2  11/2003
WO  2004027029 A2  4/2004

OTHER PUBLICATIONS

Bottoms et al, Proc. Soc. Exp. Biol. Med. 140(3):946-949, 1972; citation only.*
Mangeat et al, Nature 424:99-103, 2003.*
Pincus, Drug Discovery Today 1(1):49-56, 2004.*
Hersberger et al, Biochem. J. (369):255-262, 2003.*
GenBank Accession No. BE684372 dated Apr. 25, 2001, 2 pages.
GenBank Accession No. BI346898 dated Jul. 30, 2001, 2 pages.
GenBank Accession No. NM_145298 dated Mar. 25, 2007, 5 pages.
GenBank Accession No. NM_021822 dated Apr. 1, 2007, 4 pages.
Alce et al., "APOBEC3G Is Incorporated into Virus-like Particles by a Direct Interaction with HIV-1 Gag Nucleocapsid Protein," J. Biol. Chem., 2004, 279(33):34083-34086.
Bannert et al., "Retroelements and the human genome: New perspectives on an old relation," Proc. Natl. Acad. Sci. USA, 2004, 101(suppl. 2):14572-14579.
Barnes et al., "Repair and Genetic Consequences of Endogenous DNA Base Damage in Mammalian Cells," Annu. Rev. Genet., 2004, 3 8:445-476.
Bieniasz, "Intrinsic immunity: a front-line defense against viral attack," Nat. Immunol., 2004, 5(11):1109-1115.
Bishop et al., "Cytidine Deamination of Retroviral DNA by Diverse APOBEC Proteins," Curr. Biol., 2004, 14:1392-1396.
Bogerd et al., "APOBEC3A and APOBEC3B are potent inhibitors of LTR-retrotransposon function in human cells," Nucl. Acids Res., 2006, 34(1):89-95.
Cameron, "Recent Advances in Transgenic Technology", Molecular Biotechnology, 7:253-265 (1997).
Cen et al., "The Interaction between HIV-1 Gag and APOBEC3G," J. Biol. Chem., 2004, 279(32):33177-33184.
Chang et al., "Effective generation of transgenic pigs and mice by linker based sperm-mediated gene transfer", BMC Biotechnology, 2(5): pp. 1-13 (2002).
Cibelli et al., "Cloned Transgenic Calves Produced from Nonquiescent Fetal Fibroblasts," Science, 1998, 280:1256-1258.
Conticello et al., "Evolution of the AID/APOBEC Family of Polynucleotide (Deoxy)cytidine Deaminases," Mol. Biol. Evol., 2005, 22(2):367-377.

(Continued)

*Primary Examiner* — Kevin Hill
(74) *Attorney, Agent, or Firm* — Dardi & Herbert, PLLC; Curtis B. Herbert

(57) ABSTRACT

Transgenic pigs that express one or more non-porcine cytosine deaminases are described as well as methods of making and using such pigs.

11 Claims, 15 Drawing Sheets

(56) References Cited

OTHER PUBLICATIONS

Chui et al., "The APOBEC3 Cytidine Deaminases: An Innate Defensive Network Opposing Exogenous Retroviruses and Endogenous Retroelements", Annu. Rev. Immunl. 2008, 26:317-353, XP-002549901, (2008).
Curcio et al., "Single-step selection for Ty1 element retrotransposition," Proc. Natl. Acad. Sci. USA, 1991, 88:936-940.
Deininger et al., "Mobile elements and mammalian genome evolution," Cuff. Opin. Genet. Dev., 2003, 13:651-658.
Dinoia et al., "Altering the pathway of immunoglobulin hypermutation by inhibiting uracil-DNA glycosylase," Nature, 2002, 4 19:43-48.
Douaisi et al., "HIV-1 and MLV Gag proteins are sufficient to recruit APOBEC3G into virus-like particles," Biochem. Biophys. Res. Commun., 2004, 321:566-573.
Dutko et al., "Inhibition of a Yeast LTR Retrotransposon by Human APOBEC3 Cytidine Deaminases," Curr. Biol., 2005, 15:661-666.
Esnault et al., "APOBEC3G cytidine deaminase inhibits retrotransposition of endogenous retroviruses," Nature, 2005, 433:430-433.
Esnault et al., "Dual inhibitory effects of APOBEC family proteins on retrotransposition of mammalian endogenous retroviruses," Nucl. Acids Res. 2006, 34(5):1522-1531.
Fahrenkrug et al., "Porcine gene discovery by normalized cDNA-library sequencing and EST cluster assembly," Mamm. Genome, 2002, 13:475-478.
Felgner et al., "Enhanced Gene Delivery and Mechanism Studies with a Novel Series of Cationic Lipid Formulations," J. Biol. Chem., 1994, 269(4):2550-2561.
Fouchier et al., "Human Immunodeficiency Virus Type 1 Vif Does Not Influence Expression or Virion Incorporation of gag-,pol-, and env-Encoded Proteins," J. Virol., 1996, 70(12):8263-8269.
Gietz et al., "Studies on the Transformation of Intact Yeast Cells by the LiAc/SS-DNA/PEG Procedure," Yeast, 1995, 11:355-360.
Guatelli et al, "Isothermal, in vitro amplification of nucleic acids by a multienzyme reaction modeled after retroviral replication," Proc. Nati. Acad. Sci. USA, 1990, 87:1874-1878.
Hache et al., "The Retroviral Hypermutation Specificity of APOBEC3F and APOBEC3G Is Governed by the C-terminal DNA Cytosine Deaminase Domain," J. Biol. Chem., 2005, 280(12): 10920-10924.
Harris et al., "RNA Editing Enzyme APOBEC1 and Some of Its Homologs Can Act as DNA Mutators," Mol. Cell, 2002, 10:1247-1253.
Harris et al., "DNA Deamination Mediates Innate Immunity to Retroviral Infection," Cell, 2003, 113:803-809.
Harris et al., "Retroviral Restriction by APOBEC Proteins," Nat. Rev. Immunol., 2004, 4:868-877.
Higgins, "CLUSTAL V: Multiple Alignment of DNA and Protein Sequences," Meth. Mol. Biol., 1994,25:307-318.
Hollenberg et al., "Identification of a New Family of Tissue-Specific Basic Helix-Loop-Helix Proteins with a Two-Hybrid System," Mol. Cell. Biol., 1995, 15(7):3813-3822.
Houdebine, "Production of pharmaceutical proteins from transgenic animals," J. Biotech., 34:269-287 (1994).
Humpherys et al., "Epigenetic instability in ES cells and cloned mice", Science, 293:95-97 (2001).
Huang et al., "A genomewide screen in Saccharomyces cerevisiae for genes that suppress the accumulation of mutations," Proc. Natl. Acad. Sci. USA, 2003, 100(20):1 1529-11534.
Hyrup et al., "Peptide Nucleic Acids (PNA): Synthesis, Properties and Potential Applications," Bioorg. Med. Chem., 1996, 4(1):5-23.
Ivics et al., "Molecular Reconstruction of Sleeping Beauty, a Tcl-like Transposon from Fish, and Its Transposition in Human Cells," Cell, 1997, 91(4):501-510.
Janini Eta L., "Human Immunodeficiency Virus Type 1 DNA Sequences Genetically Damaged by Hypermutation Are Often Abundant in Patient Peripheral Blood Mononuclear Cells and May Be Generated during Near-Simultaneous Infection and Activation of CD4 T Cells," J. Virol., 2001, 75(17):7973-7986.
Jarmuz et al., "An Anthropoid-Specific Locus of Orphan C to U RNA-Editing Enzymes on Chromosome 22," Genomics, 2002, 79(3):285-296.
Jonsson et al., "Evolutionary conserved and non-conserved retrovirus restriction activities of artiodactyl APOBEC3F proteins," Nuci. Acids Res., 2006, 34(19):5683-5694.
Jonsson et al., "The Restriction of Zoonotic PERV Transmission by Human AOBEC3G", PLOS ONE 2007, 2 (9):1-8, XP-002549900.
Kay et al., "Gene therapy," Proc. Natl. Acad. Sci USA, 1997, 94:12744-12746.
Kiwaki et al., "Correction of Ornithine Transcarbamylase Deficiency in Adult spfash Mice and in OTC-Deficient Human Hepatocytes with Recombinant Adenoviruses Bearing the CAG Promoter," Hum. Gene Ther., 1996, 7(7):821-830.
Wach et al., "New Heterologous Modules for Classical or PCR-based Gene Disruptions in Saccharomyces cerevisiae," Yeast, 1994, 10:1793-1808.
Wakayama et al., "Full-term development of mice from enucleated oocytes injected with cumulus cell nuclei," Nature, 1998, 394:369-374.
Wall et al., "Transgenic dairy cattle: genetic engineering on a large scale", J. Dairy Sci., 80:2213-2224 (1997).
Wall, "Transgenic Livestock: Progress and Prospects for the Future", Theriogenology, 45:57-68 (1996).
Weiss, "Hot Prospect for New Gene Amplifier," Science, 1991, 254:1292-1293.
Wiegand et al., "A second human antiretroviral factor, APOBEC3F, is suppressed by the HIV-1 and HIV-2 Vif proteins," EMBO J., 2004, 23:2451-2458.
Wilmut et al., "Viable offspring derived from fetal and adult mammalian cells," Nature, 1997, 385:810-813.
Xu et al., "CMV-β-Actin Promoter Directs Higher Expression from an Adeno-Associated Viral Vector in the Liver than the Cytomegalovirus or Elongation Factor 1αPromoter and Results in Therapeutic Levels of Human Factor X in Mice," Hum. Gene Ther., 2001, 12(5):563-573.
Yanagimachi, "Cloning: experience from the mouse and other animals", Mol. Cell Endocrinol., 187:241-248 (2002).
Yu et al., "Induction of APOBEC3G Ubiquitination and Degradation by an HIV- 1 Vif-Cu15-SCF Complex," Science, 2003, 302:1056-1060.
Yu et al., "Selective assembly of HIV-1 Vif-Cul5-ElonginB-ElonginC E3 ubiquitin ligase complex through a novel SOCS box and upstream cysteines," Genes Dev., 2004, 18:2867-2872.
Yu et al., "Single-strand specificity of APOBEC3G accounts for minus-strand deamination of the HIV genome," Nat. Struct. Mol. Biol., 2004, 11(5):435-442.
Zennou et al., "APOBEC3G Incorporation into Human Immunodeficiency Virus Type 1 Particles," J. Virol., 2004, 78 (21):12058-12061.
Zhang et al., "The cytidine deaminase CEM 15 induces hypermutation in newly synthesized HIV-1 DNA," Nature, 2003, 424:94-98.
Zhang et al., "Rapid evolution of primate antiviral enzyme APOBEC3G," Hum. Mol. Genet., 2004, 13(6):1785-1791.
Zheng et al., "Human ZPOBEC3F Is Another Host Factor That Blocks Human Immunodeficiency Virus Type 1 Replication," J. Virol., 2004, 78(1 1):6073-6076.
'Cloning' [online]. ViaGen, 2007, [retrieved on Dec. 28, 2007]. Retrieved from the Internet: <URL: www.viagen.coni/en/our-services/cloning/, 2 pages.
Bishop, "Chromosomal insertion of foreign DNA", Reprod. Nutr. Dev. 36(6):607-618 (1998).
Chui et al., The APOBEC3 cytidine deaminases: an innate defensive network opposing exogenous retroviruses and endogenous retroelements, Annual Review of Immonology, 26:317-353 (2008).
Denning, "Deletion of the (1,3)galactosyl transferase (GGTA1) gene and the prion protein (PrP) gene in sheep", Nat. Biotech, 19(6):559-562 (Jun. 1, 2001).
Guo et al., "Protein tolerance to random amino acid change", Proc Natl. Acad Sci, 101(25): 9205-9210 (2004).
Jonsson et al., The Restriction of Zoonotic PERV Transmission by Human APOBEC3G, PLoS ONE, 2(9):1-9 (Sep. 2007).
Kuroiwa et al., "Sequential targeting of the genes encoding immunoglobulin- and prion protein in cattle", Nature Genetics 36(7):775-780 (Jul. 2004).
Moreadith et al., "Gene targeting in embryonic stem cells: the new physiology and metabolism", J. Mol. Med., 75 (3):208-216 (Mar. 1997).
Mullins et al., "Transgenesis in the rat and larger mammals", Journal of Clinical Investigation, 97(7):1557-1560 (Apr. 1, 1996).

(56) References Cited

OTHER PUBLICATIONS

Ngo et al., In Merz et al., ed. "The protein folding problem and tertiary structure prediction", Birkhauser, 1994.
Pearson, "Surviving a knockout blow", Nature, 415(6867): 8-9 (Jan. 3, 2002).
Polejaeva et al., "New advances in somatic cell nuclear transfer: application in transgenesis", Theriogenology, 53 (1):117-126 (Jan. 1, 2000).
Rudinger et al., J.A. Parsons ed. "Characteristics of the amino acids as components of a peptide hormone sequence", University Park Press, 1976, pp. 1-7.
Rulicke et al., Germ line transformation of mammals by pronuclear microinjection, Experimental Physiology, 85 (6):589-601 (2000).
Lecossier et al., "Hypermutation of HIV-1 DNA in the Absence of the Vif Protein," Science, 2003, 300:1112.
Lewis, "PCR's Competitors Are Alive and Well and Moving Rapidly Towards Commercialization," Genetic Engineering News, 1992, 12:1-3.
Li et al., "Functional Domains of APOBEC3G Required for Antiviral Activity," J. Cell. Biochem., 2004, 92:560-572.
Liddament et al., "APOBEC3F Properties and Hypermutation Preferences Indicate Activity against HIV-1 In Vivo," Curr. Biol., 2004, 14:1385-1391.
Lo, "Transformation by Iontophoretic Microinjection of DNA: Multiple Integrations Without Tandem Insertions," Mol. Cell. Biol., 1983, 3(1):1803-1814.
Luo et al., "Amino-Terminal Region of the Human Immunodeficiency Virus Type 1 Nucleocapsid Is Required for Human APOBEC3G Packaging," J. Virol., 2004, 78(21): 11841-11852.
Luria et al., "Mutations of Bacteria from Virus Sensitivity to Virus Resistance," Genetics, 1943, 28:491-511.
Mangeat et al, "Broad antiretroviral defence by human APOBEC3G through lethal editing of nascent reverse transcripts," Nature, 2003, 424:99-103.
Mariani et al., "Species-Specific Exclusion of APOBEC3G from HIV-1 Virions by Vif," Cell, 2003, 114:21-31.
Marin et al., "HIV-1 Vif protein binds the editing enzyme APOBEC3G and induces its degradation," Nat. Med., 2003, 9(11):1398-1403.
Marsischky et al., "Redundancy of Saccharomyces cerevisiae MSH3 and MSH6 in MSH2-dependent mismatch repair," Genes Dev., 1996, 10:407-420.
Mehle et al., "Phosphorylation of a novel SOCS-box regulates assembly of the HIV-1 Vif-Cul5 complex that promotes APOBEC3G degradation," Genes Dev., 2004, 18:2861-2866.
Mehle et al., "Vif Overcomes the Innate Antiviral Activity of APOBEC3G by Promoting Its Degradation in the Ubiquitin-Proteasome Pathway," J. Biol. Chem., 2004, 279(9):7792-7798.
Miskey et al., "The Frog Prince: a reconstructed transposon from Rana pipiens with high transpositional activity in vertebrate cells," Nucl. Acids Res., 2003, 31(23):6873-6881.
Mol et al., "Crystal Structure of Human Uracil-DNA Glycosylase in Complex with a Protein Inhibitor: Protein Mimicry of DNA," Cell, 1995, 82:701-708.
Navarro et al., "Recent insights into HIV-1 Vif," Cuff. Opin. Immunol., 2004, 16:477-482.
Newman et al., "Antiviral Function of APOBEC3G Can Be Dissociated from Cytidine Deaminase Activity," Curr. Biol., 2005, 15:166-170.
Nissley et al., "HIV reverse transcription in yeast," Nature, 1996, 380:30.
Nissley et al., "Hybrid Tyl/HIV-1 elements used to detect inhibitors and monitor the activity of HIV-1 reverse transcriptase," Proc. Natl. Acad. Sci. USA, 1998, 95:13905-13910.
Patience et al., "Infection of human cells by an endogenous retrovirus of pigs," Nat. Med., 1997, 3(3):282-286.
Petters et al., "Culture of Pig Embryos," J. Reprod. Fertil. Suppl., 1993, 48:61-73.
Phelps et al., "Production of α 1,3-Galactosyltransferase-Dificient Pigs," Jan. 17, 2003, Science, 299:411-414.

Polejaeva et al., "Cloned Pigs Produced by Nuclear Transfer from Adult Somatic Cells," Sep. 7, 2000, Nature, 407: 86-90.
Poltoratsky et al., "Recombinogenic Phenotype of Human Activation-Induced Cytosine Deaminase," J. Immunol., 2004, 172:4308-4313.
Prather et al., "Nuclear Transplantation in Early Pig Embryos," Biol. Reprod., 1989, 41(3):414-418.
Rattray et al., "The Roles of REV3 and RAD57 in Double-Strand-Break-Repair-Induced Mutagenesis of Saccharomyces cerevisiae," Genetics, 2002, 162:1063-1077.
Rose et al., "The viral infectivity factor (Vif) of HIV-1 unveiled," Trends Mol. Med., 2004, 10(6):291-297.
Sambrook et al., "Transfer of DNA to Nitrocellulose Filters," Molecular Cloning. A Laboratory Manual, 2nd Ed., 1989, Sections 9.37-9.52.
Sawyer et al., "Ancient Adaptive Evolution of the Primate Antiviral DNA-Editing Enzyme APOBEC3G," PLoS Biol., 2004, 2(9):1278-1285.
Schafer et al, "Specific packaging of APOBEC3G into HIV-1 virions is mediated by the nucleocapsid domain of the gag polyprotein precursor," Virology, 2004, 328:163-168.
Schumacher et al., "APOBEC3G hypermutates genomic DNA and inhibits Tyl retrotransposition in yeast," Proc. Natl. Acad. Sci. USA, 2005, 102(28):9854-9859.
Sheehy et al., "Isolation of a human gene that inhibits HIV-1 infection and is suppressed by the viral Vif protein," Nature, 2002, 418:646-650.
Simon et al., "Complementation of vf-Defective Human Inununodeficiency Virus Type 1 by Primate, but not Nonprimate, Lentivirus vif Genes," J. Virol., 1995, 69(7):4166-4172.
Simon et al., "The Vif and Gag Proteins of Human Immunodeficiency Virus Type 1 Colocalize in Infected Human T Cells," J. Virol., 1997, 71(7):5259-5267.
Smith et al., "Adenovirus mediated expression of therapeutic plasma levels of human factor IX in mice," Nat. Genet., 1993, 5:397-402.
Smith et al., "Sequence Evaluation of Four Pooled-Tissue Normalized Bovine cDNA Libraries and Construction of a Gene Index for Cattle," Gen. Res., 2001, 11(4):626-630.
Spector et al., "Construction and Isolation of Recombinant Adenoviruses with Gene Replacements," Meth. Mol. Genet., 1995, 7:31-44.
Stopak et al., "HIV-1 Vif Blocks the Antiviral Activity of APOBEC3G by Impairing Both Its Translation and Intracellular Stability," Mol. Cell, 2003, 12:591-601.
Summerton et al., "Morpholino Antisense Oligomers: Design, Preparation and Properties," Antisense Nucleic Acid Drug Dev., 1997, 7(3):187-195.
Svarovskaia et al., "Human Apolipoprotein B mRNA-editing Enzyme-catalytic Polypeptide-like 3G (APOBEC3G) Is Incorporated into HIV-1 Virions through Interactions with Viral and Nonviral RNAs," J. Biol. Chem., 2004, 279 (34):35822-35828.
Thomas et al., Taber's Cyclopedic Medical Dictionary, Philadepiphia, F. A. David Company, 1993, p. 1492-1493.
Thompson et al., "Germ Line Transmission and Expression of a Corrected HPRT Gene Produced by Gene Targeting in Embryonic Stem Cells," Cell, 1989, 56:313-321.
Turelli et al., "The Innate Antiretroviral Factor APOBEC3G Does Not Affect Human LINE-1 Retrotransposition in a Cell Culture Assay," J. Biol. Chem., 2004, 279(42):43371-43373.
Turelli et al., "Inhibition of Hepatitis B Virus Replication by APOBEC3G," Science, 2004, 303:1829.
Uchida et al., "HIV, but not murine leukemia virus, vectors mediate high efficiency gene transfer into freshly isolated G0/G1 human hematopoietic stem cells," Proc. Natl. Acad. Sci. USA, 1998, 95:11939-11944.
Van Der Putten et al., "Efficient insertion of genes into the mouse germ line via retroviral vectors," Proc. Natl. Acad. Sci. USA, 1985, 82:6148-6152.

* cited by examiner

A

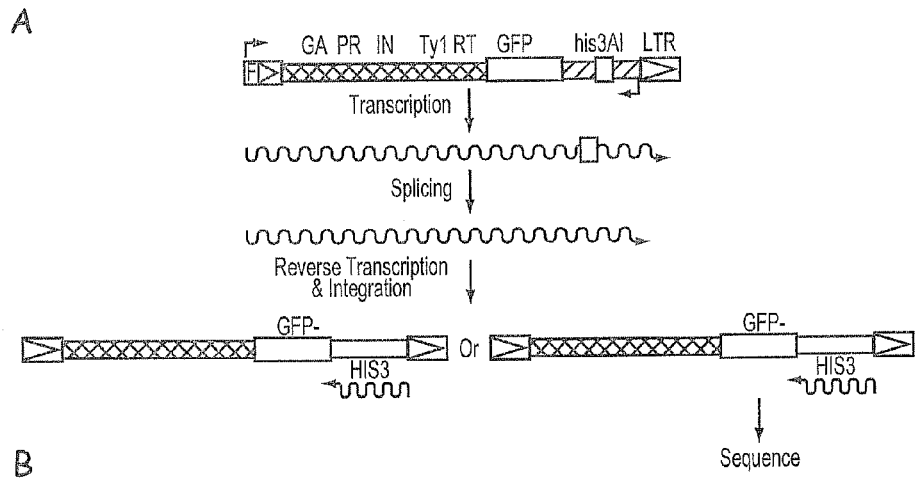

B

AAG AAA CCA ATT ATT AAA GGC TTA CTT ACT GAT AGT AGA TCA ACG ATC AGT ATA ATT AAG TCT ACA AAT GAA GAG AAA TTT AGA AAC AGA TTT 372
TTT GGC ACA AAG GCA ATG AGA CTT AGA GAT GAA GTA TCA GGT AAT AAT TTA TAC GTA TAC TAC ATC GAG ACC AAG AAG AAC ATT GCT GAT GTG 465
ATG ACA AAA CCT CTT CCG ATA AAA ACA TTT AAA CTA TTA ACT AAC AAA TGG ATT CAT TAG ATC GCG CGC GGA TCC GCC GAT TCA TTA ATG CAG 558
CTG GCA CGA CAG GTT TCC CGA CTG GAA AGC GGG CAG TGA GCG CAA CGC AAT TAA TGT GAG TTA GCT CAC TCA TTA GGC ACC CCA GGC TTT ACA 651
CTT TAT GCT TCC GGC TCG TAT GTT GTG TGG AAT TGT GAG CGG ATA ACA ATT TCA CAC AGG AAA CAG CTA TGA CCA TGA TTA CGC CAA GCT TGC 744
ATG CCT GCA GGT CGA CTC TAG AGG ATC CCC GGG TAC CGC TAG AAA AAA TGA GTA AAG GAG AAG AAC TTT TCA CTG GAG TTG TCC CAA TTC TTG 837
TTG AAT TAG ATG GTG ATG TTA ATG GGC ACA AAT TTT CTG TCA GTG GAG AGG GTG AAG GTG ATG CAA CAT ACG GAA AAC TTA CCC TTA AAT TTA 930
TTT GCA CTA CTG GAA AAC TAC CTG TTC CAT GGC CAA CAC TTG TCA CTA CTT TCT CTT ATG GTG TTC AAT GCT TTT CCC GTT ATC CGG ATC ATA 1023
TGA AAC GGC ATG ACT TTT TCA AGA GTG CCA TGC CCG AAG GTT ATG TAC AGG AAC GCA CTA TAT CTT TCA AAG ATG ACG GGA ACT ACA AGA CGC 1116
GTG CTG AAG TCA GTT TTG AAG GTG ATA CCC TTG TTA ATC GTA TCG AGT TAA AAG GTA TTG ATT TTA AAG AAG ATG GAA ACA TTC TCG GAC ACA 1209
AAC TCG AGT ACA ACT ATA ACT CAC ACA ATG TAT ACA TCA CGG CAG ACA AAC AAA AGA ATG GAA TCA AAG CTA ACT TCA AAA TTC GCC ACA ACA 1302
TTG AAG ATG GAT CCG TTC AAC TAG CAG ACC ATT ATC AAC AAA ATA CTC CAA TTG GCG ATG GCC CTG TCC TTT TAC CAG ACA ACC ATT ACC TGT 1395
CGA CAC AAT CTG CCC TTT CGA AAG ATC CCA ACG AAA AGC GTG ACC ACA TGG TCC TTC TTG AGT TTG TAA CTG CTG CTG GGA TTA CAC ATG GCA 1488
TGG ATG AGC TCT ACA AAT AAT GAA TTC CAA CTG AGC GCC GGT CGC TAC CAT TAC CAA CTT GTC TGG TGT CAA AAA TAA TAG GCC TAC TAG TCG 1581
GCC GCC GGA TCC ATC TGC AGC TTT AAA TAA TCG GTG TCA CTA CAT AAG AAC ACC TTT GGT GGA GGG AAC ATC GTT GGT ACC ATT GGG CGA GGT 1674
GGC TTC TCT TAT GGC AAC CGC AAG AGC CTT GAA CGC ACT CTC ACT ACG GTG ATG ATC ATT CTT GCC TCG CAG ACA ATC AAC GTG GAG GGT AAT 1767

Mutation to: Ⓐ ▣ ⒼAⒼ ◇

To / From

|   | A | C | G | T |
|---|---|---|---|---|
| A |   | 0 | 0 | 2 |
| C | 0 |   | 0 | 0 |
| G | 1 | 4 |   | 0 |
| T | 0 | 47 | 2 | n=56 |

B  A3G (n-47)

|   | -2 | -1 | 0 | +1 | +2 |
|---|----|----|---|----|----|
| A | 6  | 0  | 0 | 35 | 8  |
| C | 62 | 87 | 100 | 9 | 34 |
| G | 0  | 2  | 0 | 34 | 15 |
| T | 32 | 11 | 0 | 21 | 43 |

C  A3F

To / From

|   | A | C | G | T |
|---|---|---|---|---|
| A |   | 0 | 0 | 0 |
| C | 0 |   | 0 | 0 |
| G | 0 | 1 |   | 0 |
| T | 0 | 10 | 0 | n=11 |

D  A3F (n-10)

|   | -2 | -1 | 0 | +1 | +2 |
|---|----|----|---|----|----|
| A | 0  | 0  | 0 | 50 | 40 |
| C | 10 | 0  | 100 | 20 | 0 |
| G | 10 | 20 | 0 | 0 | 10 |
| T | 80 | 80 | 0 | 20 | 50 |

FIG. 9

```
BtA3F      ----------MQPAYRGYSQMPWTRDSSEHMARLDPETFYFQFCNLLYANRRNCSYIC   48
OaA3F      -------------------------MPWISDHVARLDPETFYFQFHNLLYAYGRNCSYIC   35
SsA3F      MDPQRLRQWPGPGPASRGGYGQRPRIRNPEEWFHELSPRTFSFHFRNLRFASGRNRSYIC   60
                                    .:    .*.**  *:.** :*    **  ****

BtA3F      YKVERRKYHSRASFDWGVFHNQVYGGTRCHTELRFLSWFHAEKLRPNERYHITWFMSWSP  108
OaA3F      YRVKTWKHRSPVSFDWGVFHNQVYAGTHCHSERRFLSWFCAKKLRPDECYHITWFMSWSP   95
SsA3F      CQVE-----GKNCFFQGIFQNQVPPDPPCHAELCFLSWFQSWGLSPDEHYYVTWFISWSP  115
            :*.     .   * *:*.*** .  . **:  ***** : *  **:.* *:***.****

BtA3F      CMKCAKEVADFLGRHQNVTLSIFTSRLYKFQEEGSRQGLLRLSDQGAHVDIMSYQEFKYC  168
OaA3F      CMKCAELVAGFLGMYQNVTLSIFTARLYYFQKPQYRKGLLRLSDQGACVDIMSYQEFKYC  155
SsA3F      CCECAAKVAQFLEENRNVSLSLSAARLYYFWKSESREGLRRLSDLGAQVGIMSFQDFQHC  175
           * :**  ** **  ::**:**::: **** *:: :.*.** *** **.*.***:*:*::*

BtA3F      WKKFVYSQRRPFRPWKKLDRNYQRLVEELEDILGNTMNLLREVLFKQQFGNQPRVPAPYY  228
OaA3F      WKKFVYSQRRPFRPWKKLKRNYQLLAAELEDILGNTMNLLRETLFKQQFGNQPRVPPPYY  215
SsA3F      WNNFVHNLGMPFQPWKKLHKNYQRLVTELQILRNTMNLLKENIFIQQFGNQPRVLAPYY  235
           *::**:.   **:****:.***: *. **:* *:*****::: :* .**********  ***

BtA3F      RRKTYLCYQLKQRNDLTLDRGCFRNKKQRHAEIRFIDKINSLDLNPSQSYKIICYITWSP  288
OaA3F      RRKTYLCYQLKELDDLMLDKGCFRNKKQRHAEIRFIDKINSLNLNPSQSYKIICYITWSP  275
SsA3F      LRKTYLCYQVKGPDDSILDKGCFQNKKKRHAEIRFIDKINSLNLDQNQCYRIICYVTWSP  295
            ********.*   :* :**.***:***:****************.*.* .*:****.****

BtA3F      CPNCANELVNFITRNNHLKLEIFASRLYFHWIKSFKMGLQDLQNAGISVAVMTHTEFEDC  328
OaA3F      CPNCASELVDFITRNDHLNLQIFASRLYFHWIKPFCRGLHQLQKAGISVAVMTHTEFEDC  335
SsA3F      CHNCAKELVDFISNRHHLSLQLFASRLYFHWVRCYQRGLQRLQAKRVSVAVMKGPEFKDC  355
           * *** ***:**:.:*.**.*::********:.   :**::**   :*****: **.**

BtA3F      WEQFVDNQSRPFQPWDKLEQYSASIRRRLQRILTAPI-----------------------  385
OaA3F      WEQFVDNQLRPFQPWDKLEQYSASIRRRLQRILTAPT-----------------------  372
SsA3F      WEKFVDHQGRSFPSWEKLEQYSESISRRLSRILRFANQNNLEDSFRDLRLGSPSPSSSRS  415
           **:***:*  *.*..*:*******.**:***.***  *:

BtA3F      ---
OaA3F      ---
SsA3F      DSR 418
```

FIG. 13

```
HsA3F  PETHCHAERCFLSWFCDDILSPNTNYEVTWYTSWSPCPECAGEVA 288
BtA3F  GGTRCHTELRFLSWFHAEKLRPNERYHITWFMSWSPCMKCAKEVA 117
OaA3F  AGTHCHSERRFKSWFCAKKLRPDECYHITWFMSWSPCMKCAELVA 104
SsA3F  PDPPCHAELCFLSWFQSWGLSPDEHYYVTWFISWSPCCECAAKVA 124
       HXE            X24-28              SPCXXC
```

FIG. 14

SEQUENCE LISTING

<160> NUMBER OF SEQ ID NOS: 23

<210> SEQ ID NO 1
<211> LENGTH: 1488
<212> TYPE: DNA
<213> ORGANISM: Artificial Sequence
<220> FEATURE:
<223> OTHER INFORMATION: Synthetic

<400> SEQUENCE: 1

| | | | | | |
|---|---|---|---|---|---|
| aagaaaccaa | ttattaaagg | cttacttact | gatagtagat | caacgatcag | tataattaag | 60 |
| tctacaaatg | aagagaaatt | tagaaacaga | ttttttggca | caaaggcaat | gagacttaga | 120 |
| gatgaagtat | caggtaataa | tttatacgta | tactacatcg | agaccaagaa | gaacattgct | 180 |
| gatgtgatga | caaaacctct | tccgataaaa | acatttaaac | tattaactaa | caaatggatt | 240 |
| cattagatcg | cgcgcggatc | cgccgattca | ttaatgcagc | tggcacgaca | ggtttcccga | 300 |
| ctggaaagcg | ggcagtgagc | gcaacgcaat | taatgtgagt | tagctcactc | attaggcacc | 360 |
| ccaggcttta | cactttatgc | ttccggctcg | tatgttgtgt | ggaattgtga | gcggataaca | 420 |
| atttcacaca | ggaaacagct | atgaccatga | ttacgccaag | cttgcatgcc | tgcaggtcga | 480 |
| ctctagagga | tccccgggta | ccggtagaaa | aaatgagtaa | aggagaagaa | cttttcactg | 540 |
| gagttgtccc | aattcttgtt | gaattagatg | gtgatgttaa | tgggcacaaa | ttttctgtca | 600 |
| gtggagaggg | tgaaggtgat | gcaacatacg | gaaaacttac | ccttaaattt | atttgcacta | 660 |
| ctggaaaact | acctgttcca | tggccaacac | ttgtcactac | tttctcttat | ggtgttcaat | 720 |
| gcttttcccg | ttatccggat | catatgaaac | ggcatgactt | tttcaagagt | gccatgcccg | 780 |
| aaggttatgt | acaggaacgc | actatatctt | tcaaagatga | cgggaactac | aagacgcgtg | 840 |
| ctgaagtcaa | gtttgaaggt | gatacccttg | ttaatcgtat | cgagttaaaa | ggtattgatt | 900 |
| ttaaagaaga | tggaaacatt | ctcggacaca | aactcgagta | caactataac | tcacacaatg | 960 |
| tatacatcac | ggcagacaaa | caaaagaatg | gaatcaaagc | taacttcaaa | attcgccaca | 1020 |
| acattgaaga | tggatccgtt | caactagcag | accattatca | acaaaatact | ccaattggcg | 1080 |
| atggccctgt | cctttaccca | gacaaccatt | acctgtcgac | acaatctgcc | ctttcgaaag | 1140 |
| atcccaacga | aaagcgtgac | cacatggtcc | ttcttgagtt | tgtaactgct | gctgggatta | 1200 |
| cacatggcat | ggatgagctc | tacaaataat | gaattccaac | tgagcgccgg | tcgctaccat | 1260 |
| taccaacttg | tctggtgtca | aaaataatag | gcctactagt | cggcgcgcgg | atccatctgc | 1320 |
| agctttaaat | aatcggtgtc | actacataag | aacacctttg | gtggagggaa | catcgttggt | 1380 |
| accattgggc | gaggtggctt | ctcttatggc | aaccgcaaga | gccttgaacg | cactctcact | 1440 |
| acggtgatga | tcattcttgc | ctcgcagaca | atcaacgtgg | agggtaat | | 1488 |

<210> SEQ ID NO 2
<211> LENGTH: 18
<212> TYPE: DNA
<213> ORGANISM: Artificial Sequence
<220> FEATURE:
<223> OTHER INFORMATION: Primer

<400> SEQUENCE: 2
cctgagtggg agttgtta                                                       18

<210> SEQ ID NO 3
<211> LENGTH: 21
<212> TYPE: DNA
<213> ORGANISM: Artificial Sequence

```
<220> FEATURE:
<223> OTHER INFORMATION: Primer

<400> SEQUENCE: 3
tatgatacat gctctggcca a                                        21

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gtctgcgagg caagaatgat                                          20

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
cgttatccgg atcatatga                                           19

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
gtagttcccg tcatcttga                                           19

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
agatgggcac agtgtgggt                                           19

<210> SEQ ID NO 8
<211> LENGTH: 385
<212> TYPE: PRT
<213> ORGANISM: Bos Taurus

<400> SEQUENCE: 8
```

| Met | Gln | Pro | Ala | Tyr | Arg | Gly | Tyr | Ser | Gln | Met | Pro | Trp | Thr | Arg | Asp |
|---|---|---|---|---|---|---|---|---|---|---|---|---|---|---|---|
| 1 |  |  |  | 5 |  |  |  |  | 10 |  |  |  |  | 15 |  |

| Ser | Ser | Glu | His | Met | Ala | Arg | Leu | Asp | Pro | Glu | Thr | Phe | Tyr | Phe | Gln |
|---|---|---|---|---|---|---|---|---|---|---|---|---|---|---|---|
|  |  |  | 20 |  |  |  |  | 25 |  |  |  |  | 30 |  |  |

| Phe | Cys | Asn | Leu | Leu | Tyr | Ala | Asn | Arg | Arg | Asn | Cys | Ser | Tyr | Ile | Cys |
|---|---|---|---|---|---|---|---|---|---|---|---|---|---|---|---|
|  |  | 35 |  |  |  |  | 40 |  |  |  |  | 45 |  |  |  |

| Tyr | Lys | Val | Glu | Arg | Arg | Lys | Tyr | His | Ser | Arg | Ala | Ser | Phe | Asp | Trp |
|---|---|---|---|---|---|---|---|---|---|---|---|---|---|---|---|
|  | 50 |  |  |  |  | 55 |  |  |  |  | 60 |  |  |  |  |

| Gly | Val | Phe | His | Asn | Gln | Val | Tyr | Gly | Gly | Thr | Arg | Cys | His | Thr | Glu |
|---|---|---|---|---|---|---|---|---|---|---|---|---|---|---|---|
| 65 |  |  |  |  | 70 |  |  |  |  | 75 |  |  |  |  | 80 |

| Leu | Arg | Phe | Leu | Ser | Trp | Phe | His | Ala | Glu | Lys | Leu | Arg | Pro | Asn | Glu |
|---|---|---|---|---|---|---|---|---|---|---|---|---|---|---|---|

```
                      85                  90                  95
Arg Tyr His Ile Thr Trp Phe Met Ser Trp Ser Pro Cys Met Lys Cys
                100                 105                 110

Ala Lys Glu Val Ala Asp Phe Leu Gly Arg His Gln Asn Val Thr Leu
                115                 120                 125

Ser Ile Phe Thr Ser Arg Leu Tyr Lys Phe Gln Glu Glu Gly Ser Arg
                130                 135                 140

Gln Gly Leu Leu Arg Leu Ser Asp Gln Gly Ala His Val Asp Ile Met
145                 150                 155                 160

Ser Tyr Gln Glu Phe Lys Tyr Cys Trp Lys Lys Phe Val Tyr Ser Gln
                165                 170                 175

Arg Arg Pro Phe Arg Pro Trp Lys Lys Leu Asp Arg Asn Tyr Gln Arg
                180                 185                 190

Leu Val Glu Glu Leu Glu Asp Ile Leu Gly Asn Thr Met Asn Leu Leu
                195                 200                 205

Arg Glu Val Leu Phe Lys Gln Gln Phe Gly Asn Gln Pro Arg Val Pro
                210                 215                 220

Ala Pro Tyr Tyr Arg Arg Lys Thr Tyr Leu Cys Tyr Gln Leu Lys Gln
225                 230                 235                 240

Arg Asn Asp Leu Thr Leu Asp Arg Gly Cys Phe Arg Asn Lys Lys Gln
                245                 250                 255

Arg His Ala Glu Ile Arg Phe Ile Asp Lys Ile Asn Ser Leu Asp Leu
                260                 265                 270

Asn Pro Ser Gln Ser Tyr Lys Ile Ile Cys Tyr Ile Thr Trp Ser Pro
                275                 280                 285

Cys Pro Asn Cys Ala Asn Glu Leu Val Asn Phe Ile Thr Arg Asn Asn
290                 295                 300

His Leu Lys Leu Glu Ile Phe Ala Ser Arg Leu Tyr Phe His Trp Ile
                305                 310                 315                 320

Lys Ser Phe Lys Met Gly Leu Gln Asp Leu Gln Asn Ala Gly Ile Ser
                325                 330                 335

Val Ala Val Met Thr His Thr Glu Phe Glu Asp Cys Trp Glu Gln Phe
                340                 345                 350

Val Asp Asn Gln Ser Arg Pro Phe Gln Pro Trp Asp Lys Leu Glu Gln
                355                 360                 365

Tyr Ser Ala Ser Ile Arg Arg Leu Gln Arg Ile Leu Thr Ala Pro
                370                 375                 380

Ile
385

<210> SEQ ID NO 9
<211> LENGTH: 372
<212> TYPE: PRT
<213> ORGANISM: Ovis aries

<400> SEQUENCE: 9

Met Pro Trp Ile Ser Asp His Val Ala Arg Leu Asp Pro Glu Thr Phe
1               5                   10                  15

Tyr Phe Gln Phe His Asn Leu Leu Tyr Ala Tyr Gly Arg Asn Cys Ser
                20                  25                  30

Tyr Ile Cys Tyr Arg Val Lys Thr Trp Lys His Arg Ser Pro Val Ser
                35                  40                  45

Phe Asp Trp Gly Val Phe His Asn Gln Val Tyr Ala Gly Thr His Cys
                50                  55                  60
```

```
His Ser Glu Arg Arg Phe Leu Ser Trp Phe Cys Ala Lys Lys Leu Arg
 65                  70                  75                  80

Pro Asp Glu Cys Tyr His Ile Thr Trp Phe Met Ser Trp Ser Pro Cys
                 85                  90                  95

Met Lys Cys Ala Glu Leu Val Ala Gly Phe Leu Gly Met Tyr Gln Asn
            100                 105                 110

Val Thr Leu Ser Ile Phe Thr Ala Arg Leu Tyr Tyr Phe Gln Lys Pro
        115                 120                 125

Gln Tyr Arg Lys Gly Leu Leu Arg Leu Ser Asp Gln Gly Ala Cys Val
    130                 135                 140

Asp Ile Met Ser Tyr Gln Glu Phe Lys Tyr Cys Trp Lys Lys Phe Val
145                 150                 155                 160

Tyr Ser Gln Arg Arg Pro Phe Arg Pro Trp Lys Lys Leu Lys Arg Asn
                165                 170                 175

Tyr Gln Leu Leu Ala Ala Glu Leu Glu Asp Ile Leu Gly Asn Thr Met
            180                 185                 190

Asn Leu Leu Arg Glu Thr Leu Phe Lys Gln Gln Phe Gly Asn Gln Pro
        195                 200                 205

Arg Val Pro Pro Pro Tyr Tyr Arg Arg Lys Thr Tyr Leu Cys Tyr Gln
    210                 215                 220

Leu Lys Glu Leu Asp Asp Leu Met Leu Asp Lys Gly Cys Phe Arg Asn
225                 230                 235                 240

Lys Lys Gln Arg His Ala Glu Ile Arg Phe Ile Asp Lys Ile Asn Ser
                245                 250                 255

Leu Asn Leu Asn Pro Ser Gln Ser Tyr Lys Ile Ile Cys Tyr Ile Thr
            260                 265                 270

Trp Ser Pro Cys Pro Asn Cys Ala Ser Glu Leu Val Asp Phe Ile Thr
        275                 280                 285

Arg Asn Asp His Leu Asn Leu Gln Ile Phe Ala Ser Arg Leu Tyr Phe
    290                 295                 300

His Trp Ile Lys Pro Phe Cys Arg Gly Leu His Gln Leu Gln Lys Ala
305                 310                 315                 320

Gly Ile Ser Val Ala Val Met Thr His Thr Glu Phe Glu Asp Cys Trp
                325                 330                 335

Glu Gln Phe Val Asp Asn Gln Leu Arg Pro Phe Gln Pro Trp Asp Lys
            340                 345                 350

Leu Glu Gln Tyr Ser Ala Ser Ile Arg Arg Leu Gln Arg Ile Leu
        355                 360                 365

Thr Ala Pro Thr
    370

<210> SEQ ID NO 10
<211> LENGTH: 418
<212> TYPE: PRT
<213> ORGANISM: Sus scrofa

<400> SEQUENCE: 10

Met Asp Pro Gln Arg Leu Arg Gln Trp Pro Gly Pro Gly Pro Ala Ser
1                5                  10                  15

Arg Gly Gly Tyr Gly Gln Arg Pro Arg Ile Arg Asn Pro Glu Glu Trp
             20                  25                  30

Phe His Glu Leu Ser Pro Arg Thr Phe Ser Phe His Phe Arg Asn Leu
         35                  40                  45

Arg Phe Ala Ser Gly Arg Asn Arg Ser Tyr Ile Cys Cys Gln Val Glu
    50                  55                  60
```

Gly Lys Asn Cys Phe Phe Gln Gly Ile Phe Gln Asn Gln Val Pro Pro
65                  70                  75                  80

Asp Pro Pro Cys His Ala Glu Leu Cys Phe Leu Ser Trp Phe Gln Ser
            85                  90                  95

Trp Gly Leu Ser Pro Asp Glu His Tyr Tyr Val Thr Trp Phe Ile Ser
            100                 105                 110

Trp Ser Pro Cys Cys Glu Cys Ala Ala Lys Val Ala Gln Phe Leu Glu
            115                 120                 125

Glu Asn Arg Asn Val Ser Leu Ser Leu Ser Ala Ala Arg Leu Tyr Tyr
            130                 135                 140

Phe Trp Lys Ser Glu Ser Arg Glu Gly Leu Arg Arg Leu Ser Asp Leu
145                 150                 155                 160

Gly Ala Gln Val Gly Ile Met Ser Phe Gln Asp Phe Gln His Cys Trp
                165                 170                 175

Asn Asn Phe Val His Asn Leu Gly Met Pro Phe Gln Pro Trp Lys Lys
            180                 185                 190

Leu His Lys Asn Tyr Gln Arg Leu Val Thr Glu Leu Lys Gln Ile Leu
            195                 200                 205

Arg Asn Thr Met Asn Leu Leu Lys Glu Asn Ile Phe Ile Gln Gln Phe
210                 215                 220

Gly Asn Gln Pro Arg Val Leu Ala Pro Tyr Tyr Leu Arg Lys Thr Tyr
225                 230                 235                 240

Leu Cys Tyr Gln Val Lys Gly Pro Asp Asp Ser Ile Leu Asp Lys Gly
            245                 250                 255

Cys Phe Gln Asn Lys Lys Lys Arg His Ala Glu Ile Arg Phe Ile Asp
            260                 265                 270

Lys Ile Asn Ser Leu Asn Leu Asp Gln Asn Gln Cys Tyr Arg Ile Ile
            275                 280                 285

Cys Tyr Val Thr Trp Ser Pro Cys His Asn Cys Ala Lys Glu Leu Val
290                 295                 300

Asp Phe Ile Ser Asn Arg His His Leu Ser Leu Gln Leu Phe Ala Ser
305                 310                 315                 320

Arg Leu Tyr Phe His Trp Val Arg Cys Tyr Gln Arg Gly Leu Gln Arg
            325                 330                 335

Leu Gln Ala Lys Arg Val Ser Val Ala Val Met Lys Gly Pro Glu Phe
            340                 345                 350

Lys Asp Cys Trp Glu Lys Phe Val Asp His Gln Gly Arg Ser Phe Pro
            355                 360                 365

Ser Trp Glu Lys Leu Glu Gln Tyr Ser Glu Ser Ile Ser Arg Arg Leu
            370                 375                 380

Ser Arg Ile Leu Arg Phe Ala Asn Gln Asn Asn Leu Glu Asp Ser Phe
385                 390                 395                 400

Arg Asp Leu Arg Leu Gly Ser Pro Ser Pro Ser Ser Ser Arg Ser Asp
                405                 410                 415

Ser Arg

<210> SEQ ID NO 11
<211> LENGTH: 45
<212> TYPE: PRT
<213> ORGANISM: Homo sapien

<400> SEQUENCE: 11

Pro Glu Thr His Cys His Ala Glu Arg Cys Phe Leu Ser Trp Phe Cys
1               5                   10                  15

```
Asp Asp Ile Leu Ser Pro Asn Thr Asn Tyr Glu Val Thr Trp Tyr Thr
            20                  25                  30

Ser Trp Ser Pro Cys Pro Glu Cys Ala Gly Glu Val Ala
            35                  40              45

<210> SEQ ID NO 12
<211> LENGTH: 45
<212> TYPE: PRT
<213> ORGANISM: Bos taurus

<400> SEQUENCE: 12

Gly Gly Thr Arg Cys His Thr Glu Leu Arg Phe Leu Ser Trp Phe His
1               5                   10                  15

Ala Glu Lys Leu Arg Pro Asn Glu Arg Tyr His Ile Thr Trp Phe Met
            20                  25                  30

Ser Trp Ser Pro Cys Met Lys Cys Ala Lys Glu Val Ala
            35                  40              45

<210> SEQ ID NO 13
<211> LENGTH: 45
<212> TYPE: PRT
<213> ORGANISM: Ovis aries

<400> SEQUENCE: 13

Ala Gly Thr His Cys His Ser Glu Arg Arg Phe Lys Ser Trp Phe Cys
1               5                   10                  15

Ala Lys Lys Leu Arg Pro Asp Glu Cys Tyr His Ile Thr Trp Phe Met
            20                  25                  30

Ser Trp Ser Pro Cys Met Lys Cys Ala Glu Leu Val Ala
            35                  40              45

<210> SEQ ID NO 14
<211> LENGTH: 45
<212> TYPE: PRT
<213> ORGANISM: Sus scrofa

<400> SEQUENCE: 14

Pro Asp Pro Pro Cys His Ala Glu Leu Cys Phe Leu Ser Trp Phe Gln
1               5                   10                  15

Ser Trp Gly Leu Ser Pro Asp Glu His Tyr Tyr Val Thr Trp Phe Ile
            20                  25                  30

Ser Trp Ser Pro Cys Cys Glu Cys Ala Ala Lys Val Ala
            35                  40              45

<210> SEQ ID NO 15
<211> LENGTH: 21
<212> TYPE: DNA
<213> ORGANISM: Artificial Seqeunce
<220> FEATURE:
<223> OTHER INFORMATION: Primer

<400> SEQUENCE: 15
ttcatgtggg acactagaga t                                           21

<210> SEQ ID NO 16
<211> LENGTH: 23
<212> TYPE: DNA
<213> ORGANISM: Artificial Seqence
<220> FEATURE:
<223> OTHER INFORMATION: Primer

<400> SEQUENCE: 16
```
aaccctttac cctttatgtg gat          23

<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
aaagtcaatt tgtcagcgtc ctt          23

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
ggaacctgca acctatggaa              20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
ggtgtggccc taaaaagaca              20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
atcatgtttg agaccttcaa              20

<210> SEQ ID NO 21
<211> LENGTH: 13
<212> TYPE: DNA
<213> ORGANISM: Homo Sapien

<400> SEQUENCE: 21
tcgtcccagt aaa                     13

<210> SEQ ID NO 22
<211> LENGTH: 13
<212> TYPE: DNA
<213> ORGANISM: Artificial Sequence
<220> FEATURE:
<223> OTHER INFORMATION: Synthetic

<400> SEQUENCE: 22
gtcgyccagg agg                     13

<210> SEQ ID NO 23
<211> LENGTH: 13
<212> TYPE: DNA
<213> ORGANISM: Artificial Sequence
<220> FEATURE:

```
<223> OTHER INFORMATION: Synthetic

<400> SEQUENCE: 23
gtagyccagg gtg                                                              13
```

USING CYTOSINE DEAMINASES TO DIMINISH RETROELEMENT TRANSFER FROM PIGS TO HUMANS

CROSS REFERENCE TO RELATED APPLICATIONS

This application a continuation of U.S. patent application Ser. No. 12/243,711, filed Oct. 1, 2001, which is a continuation of U.S. application Ser. No. 11/472,743, filed Jun. 22, 2006, which claims the benefit of U.S. Provisional Application No. 60/694,054, filed Jun. 24, 2005, each of which are hereby incorporated by reference herein in their entirety.

TECHNICAL FIELD

This invention relates to transgenic pigs and porcine cells that have decreased capability of transmitting retroelements such as porcine endogenous retroviruses to non-porcine cells and tissues, and more particularly to transgenic pigs and porcine cells that contain non-porcine cytosine deaminases.

BACKGROUND

Treating diabetes remains a substantial burden for patients and their families, with up to 50% of patients experiencing devastating secondary complications due to a lifetime of exposure to elevated glucose levels. Currently the only way to restore and sustain insulin without the associated risk of hyper- or hypoglycemia is to replace the patient's insulin-producing cells, the islets of Langerhans: either by the transplant of a vascularized pancreas or by the infusion of isolated islets. However, suitable human pancreas donors are very rare. Pigs provide a potentially unlimited source of islets for xenotransplantation to diabetic patients, and can be developed to the point of clinical applicability, potentially well before other developing technologies, such as stein cells.

The potential for transmission of viruses from the donor to host tissue remains an impediment to the use of xenotransplantation for the treatment of diabetes. Although rigorous biosecurity and testing can eliminate most agents from potential donor pigs, one agent in particular is recalcitrant to this approach. Most, perhaps all, vertebrate genomes, infections. Although most of these are functionally inactive, pig cells contain several types of ACTIVE retroelements called porcine endogenous retroviruses (PERVs). These agents are generally innocuous to the pig, but are of major concern for xenotransplantation. Under laboratory conditions in which human and pig cells are co-cultured, transmission of PERVs from pig to human tissue has been demonstrated (Patience et al. (1997) *Nat Med* 3, 282-286). It is unclear what, if any ramifications this transmission would have for a patient, but the theorized possibility that PERVs alone or in combination with human agents could cause disease has emerged as a major hurdle to the widespread application of xenotransplantation.

SUMMARY

The invention is based on the expression of non-porcine cytosine deaminase polypeptides in pig cells and tissues. As described herein, expression of non-porcine cytosine deaminases (e.g., human cytosine deaminases) in porcine cells and tissues can facilitate control of the transmission of retroelements such as PERVs to human cells. As a result, pigs cells and tissues that contain non-porcine cytosine deaminases have reduced capability of transmitting PERVs to human cells and as such, can reduce the risks associated with xenotransplantation from cross species gene transfer.

In one aspect, the invention features a nucleic acid construct that includes a transcriptional unit, the transcriptional unit including a porcine regulatory region operably linked to a nucleic acid sequence encoding a non-porcine cytosine deaminase polypeptide. An inverted repeat of a transposon can flank each side of the transcriptional unit. An insulator element also can flank each side of the transcriptional unit. The nucleic acid construct further can include a nucleic acid sequence encoding a transposase.

The cytosine deaminase polypeptide can be selected from the group consisting of AID, APOBEC1, APOBEC2, APOBEC3A, APOBEC3B, APOBEC3C, APOBEC3D, APOBEC3E, APOBEC3F, APOBEC3G, and APOBEC3H. For example, the cytosine deaminase polypeptide can be an APOBEC3F polypeptide such as a human APOBEC3F polypeptide or can be an APOBEC3G polypeptide such as a human APOBEC3G polypeptide. In some embodiments, the nucleic acid sequence encodes at least two cytosine deaminase polypeptides (e.g., an APOBEC3F polypeptide and an APOBEC3G polypeptide). The porcine regulatory region can be a constitutive promoter or a tissue-specific promoter.

In another aspect, the invention features an isolated porcine cell that includes a nucleic acid construct, the nucleic acid construct including a regulatory region operably linked to a nucleic acid sequence encoding a non-porcine cytosine deaminase polypeptide. The cell can be an embryonic cell, a fetal porcine cell (e.g., a fibroblast), an adult porcine cell (e.g., a dermal fibroblast), a germ cell (e.g., an oocyte or an egg), a stem cell (e.g., an adult stem cell or an embryonic stem cell), or a progenitor cell.

The invention also features an isolated porcine cell that includes a non-porcine cytosine deaminase. The cell further can include a nucleic acid encoding the non-porcine cytosine deaminase. The cytosine deaminase polypeptide can be selected from the group consisting of AID, APOBEC1, APOBEC2, APOBEC3A, APOBEC3B, APOBEC3C, APOBEC3D, APOBEC3E, APOBEC3F, APOBEC3G, and APOBEC3H. For example, the cytosine deaminase polypeptide can be an APOBEC3F polypeptide such as a human APOBEC3F polypeptide or can be an APOBEC3G polypeptide such as a human APOBEC3G polypeptide. In some embodiments, the nucleic acid sequence encodes at least two cytosine deaminase polypeptides (e.g., an APOBEC3F polypeptide and an APOBEC3G polypeptide). The regulatory region can be a constitutive promoter or a tissue-specific promoter.

In another aspect, the invention features a transgenic pig, cells derived from the transgenic pig, tissue isolated from the transgenic pig, and progeny of the transgenic pig. The nucleated cells of the pig include a nucleic acid construct, which includes a transcriptional unit that includes a regulatory region operably linked to a nucleic acid sequence encoding a non-porcine cytosine deaminase polypeptide. Expression of the non-porcine cytosine deaminase polypeptide in at least some of the cells of the pig results, upon co-culture with human cells, in decreased capability of the cells to transmit porcine endogenous retroviruses to the human cells. The regulatory region can be a constitutive promoter or a tissue-specific promoter. An insulator element and an inverted repeat of a transposon can flank each side of the transcriptional unit. The cytosine deaminase polypeptide can be selected from the group consisting of AID, APOBEC1, APOBEC2, APOBEC3A, APOBEC3B, APOBEC3C, APOBEC3D, APOBEC3E, APOBEC3F, APOBEC3G, and APOBEC3H. For example, the cytosine deaminase polypeptide can be an APOBEC3F polypeptide such as a human APOBEC3F polypeptide or can be an APOBEC3G polypeptide such as a human APOBEC3G polypeptide.

In another aspect, the invention features a method for making a transgenic pig. The method includes introducing a transgenic pig cell into an enucleated pig oocyte to establish a combined cell, the transgenic pig cell includes a nucleic acid construct, which includes a transcriptional unit that includes a regulatory region operably linked to a nucleic acid sequence encoding a non-porcine cytosine deaminase polypeptide; producing a porcine embryo from the combined cell; transferring the porcine embryo to a recipient female; and allowing the porcine embryo to develop in the recipient female to produce the transgenic pig. An insulator element and an inverted repeat of a transposon can flank each side of the transcriptional unit.

The invention also features a method of making a transgenic pig. The method includes introducing a nucleic acid construct into a fertilized egg to produce an injected fertilized egg, where the nucleic acid construct includes a transcriptional unit that includes a regulatory region operably linked to a nucleic acid sequence encoding a non-porcine cytosine deaminase polypeptide; transferring the injected fertilized egg to a recipient female; and allowing the injected fertilized egg to develop in the recipient porcine female to produce the transgenic pig.

In yet another aspect, the invention features a method for making a transgenic pig cell. The method includes introducing a nucleic acid construct into a pig cell, the nucleic acid construct including a regulatory region operably linked to a nucleic acid sequence encoding a non-porcine cytosine deaminase polypeptide.

The invention also features a method for making a transgenic pig cell. The method includes introducing into a pig cell: a) a nucleic acid construct that includes a transcriptional unit, the transcriptional unit including a regulatory region operably linked to a nucleic acid sequence encoding a non-porcine cytosine deaminase polypeptide, wherein an insulator element and an inverted repeat of a transposon flank each side of the transcriptional unit; and b) a source of a transposase. The source of the transposase can include a nucleic acid encoding the transposase. The transposon and the source of transposase can be present on separate nucleic acid constructs or on the same nucleic acid construct.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 2 is a histogram summarizing the APOBEC3G-dependent CAN1 mutator phenotype from seven independent experiments, each performed with 6-8 independent yeast cultures expressing APOBEC3G or a control vector. The average of the median mutation frequencies and the corresponding SEMs are shown. The average median mutation frequency of yeast expressing the vector control was $1.3 \times 10^{-6}$; this number was assigned a value of one to normalize and highlight the magnitude of the APOBEC3G mutator phenotype (33-fold). Data from FIGS. 1A and 1B, and FIG. 3 are included with data from three additional experiments. The variation in values among individual cultures for each experiment and among the median values of the seven experiments is expected from the stochastic appearance of $Can^R$ mutants in the growing cultures.

FIG. 8A-8B indicate that APOBEC3F and APOBEC3G induced Ty1 cDNA hypermutations. (A) A schematic depicting the LTR-dependent His+ retrotransposition of Ty1 harboring a GFP passenger gene. His+ retrotransposition events were pooled and the GFP-negative variants were recovered for DNA sequencing as described in the Materials and Methods. GA, PR, IN, RT and LTR represent gag, protease, integrase, reverse transcriptase and long-terminal repeat, respectively. (B) A schematic showing all of the genomic (plus) strand base substitution mutations that were found in the GFP passenger gene (and surrounding regions) (SEQ ID NO:1) of His+/GFP− retrotransposons. Mutations attributable to APOBEC3G or -3F expression are indicated above and below the 1488 bp consensus sequence, respectively. The GFP start codon is underlined. All of the mutations were recovered from Ty1 experiments, except three G→A substitutions, which were from TyHRT experiments (one due to APOBEC3F is shown at consensus position 681; a second due to APOBEC3F and one due to APOBEC3G are not illustrated because they occurred in HIV RT sequence). All of these raw sequencing data are summarized in FIG. 9. Four GFP-negative controls were observed. Two were not recovered by PCR and two produced smaller PCR products and were not sequenced (likely deletions).

FIG. 9 are tables indicating the mutational preferences of APOBEC3G and APOBEC3F in Ty1 cDNA. (A, C) Summaries of the GFP gene (and surrounding region) base substitution mutations observed in pools of His+ retrotranspositions, which had occurred in the presence of APOBEC3G or -3F, respectively. (B, D) Base preferences surrounding the Ty1 cDNA C→T transition sites attributable to expression of APOBEC3G or -3F, respectively. APOBEC3G shows a clear preference for 5'-YC$\underline{C}$, whereas APOBEC3F prefers 5'-TT$\underline{C}$ (Y=C or T; the mutated cytosine is underlined).

FIG. 13 is a sequence alignment of the cow (BtA3F, SEQ ID NO:8), sheep (OaA3F, SEQ ID NO:9), and pig (SsA3F, SEQ ID NO:10) APOBEC3F proteins FIG. 14 is a sequence alignment of the active site of the human (HsA3F, SEQ ID NO:11), cow (BtA3F, SEQ ID NO:12), sheep (OaA3F, SEQ ID NO:13), and pig (SsA3F, SEQ ID NO:14) APOBEC3F proteins. The conserved motifs are boxed.

DETAILED DESCRIPTION

Figure 1:
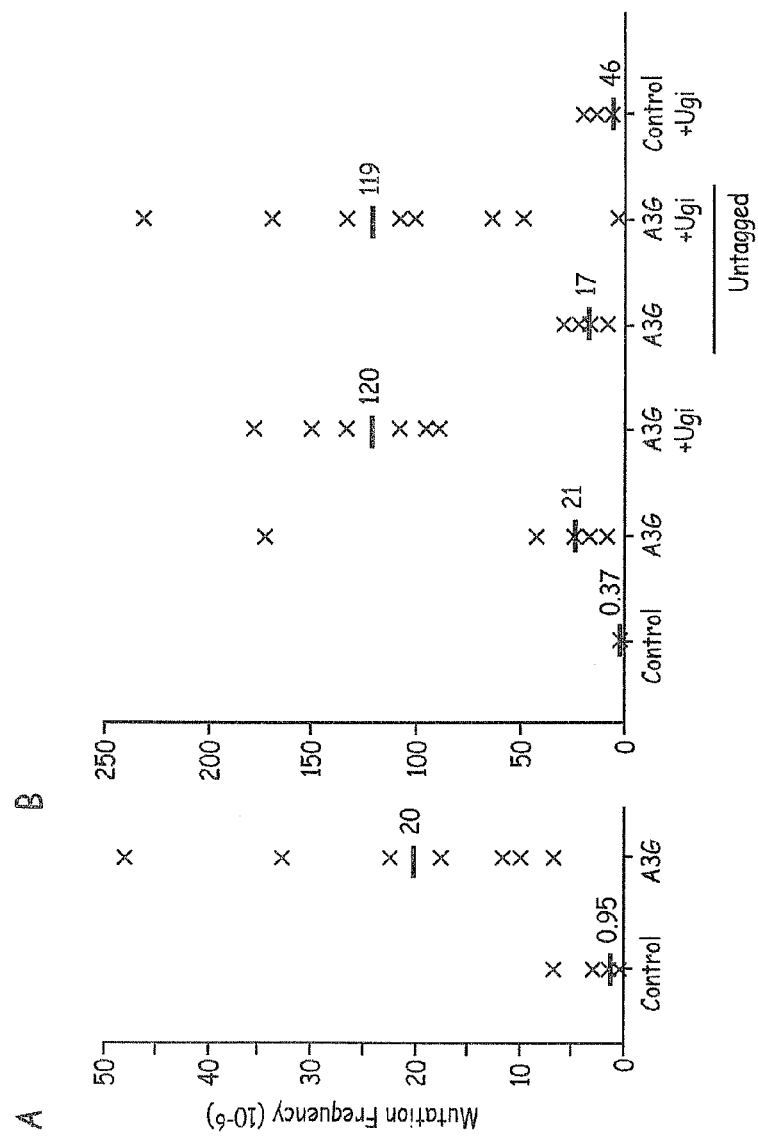
FIGS. 1A and 1B are histograms that indicate APOBEC3G stimulates mutation in S. cerevisiae by the uracil excision pathway. (A) APOBEC3G expression causes an increase in the median frequency of mutation to $Can^R$. Each X represents the frequency derived from an independent culture and the median is indicated. The Y-axis reports the observed number of $Can^R$ colonies per million viable yeast cells. Yeast expressing the control vector showed a frequency of spontaneous mutation to $Can^R$ similar to that reported previously (Huang et al. (2003) Proc Natl Acad Sci USA 100, 11529-34; Rattray et al. (2002) Genetics 162, 1063-77). The data are representative of seven independent experiments.

As described herein, human cytosine deaminases such as APOBEC3G and 3F are capable of deaminating the genomic DNA of a eukaryotic cell. Expression of APOBEC3G or its homolog APOBEC3F can inhibit the mobility of the retrotransposon Ty1 in *Saccharomyces cerevisiae* by a mechanism involving the deamination of cDNA cytosines. This expands the range of cytosine deaminase targets to include nuclear DNA and endogenous retroelements, which have pathological and physiological implications, respectively. These data indicate that the APOBEC3-dependent mechanism of retroelement restriction is highly conserved and that the range of APOBEC3 substrates may be far broader than originally anticipated. Because the APOBEC3 proteins do not exist outside of mammals, the results described herein showing that APOBEC3F or -3G can inhibit yeast Ty1 retrotransposition were unexpected. Therefore, the Ty1 data described herein not only demonstrate the remarkable conservation of this mechanism but, importantly, they also show that mammalian factors (in addition to APOBEC3F or -3G) are not required for retroelement restriction.

Furthermore, as demonstrated herein, expression of human cytosine deaminases in porcine cells reduces the capability of the porcine cells to transmit endogenous retroelements (e.g., retroviruses and retrotransposons) to the human cells. Thus, the invention provides transgenic pigs and pig cells that express a non-porcine cytosine deaminase polypeptide. Organs and tissues from such transgenic pigs are useful for xenotransplantation due to the decreased risk of transmitting the endogenous porcine retroviruses to human cells relative to organs and tissues from pigs expressing endogenous cytosine deaminases.

Non-Porcine Cytosine Deaminases

As used herein, "cytosine deaminase polypeptide" refers to any chain of amino acids, regardless of post-translational modification, that has the ability to deaminate cytosines to uracils within nucleic acid and that contains the following zinc-binding cytosine deaminase domain (amino acids provided in standard one-letter terminology): H/CXE (or another catalytic residue, e.g., D) $X_{20-30}PCX_{2-4}C$. See, Harris and Liddament (2004) *Nat. Rev. Immunol.* 4:868-877. Amino acid substitutions, deletions, and insertions can be introduced into a known zinc-binding cytosine deaminase domain and the resulting polypeptide is a "cytosine deaminase" provided that the polypeptide retains the ability to deaminate cytosines to uracils.

Suitable non-porcine, mammalian cytosine deaminase polypeptides include single domain DNA cytosine deaminases and double domain DNA cytosine deaminases. For example, single domain DNA cytosine deaminases include, for example, activation induced deaminase (AID), APOBEC1, APOBEC2, APOBEC3A, APOBEC3C, APOBEC3D, APOBEC3E, and APOBEC3H polypeptides. Double domain DNA cytosine deaminases include, for example, APOBEC3B, APOBEC3F, and APOBEC3G polypeptides. APOBEC3D and APOBEC3E also can be produced as double domain cytosine deaminases. See, e.g., Harris and Liddament (2004), supra; and Jarmuz et al *Genomics* (2002) 79(3):285-96. APOBEC3G and/or APOBEC3F are particularly useful. Human APOBEC3G (apolipoprotein B mRNA-editing enzyme catalytic polypeptide-like 3G, also known as CEM15) uses cytosine to uracil deamination to inhibit the replication of a variety of retroviruses, including HIV-1. APOBEC3G localizes predominantly to the cytoplasm of mammalian cells. In a retrovirus-infected cell, this localization may facilitate the incorporation of APOBEC3G into viral particles, which are released from the plasma membrane. APOBEC3G also is specifically incorporated into virions through an association with the viral Gag protein and/or viral genomic RNA. Once a retrovirus enters a cell, its genomic RNA is reverse transcribed, and during this process, APOBEC3G is capable of deaminating cDNA cytosines to uracils (C→U). These lesions occur at such a high frequency that they ultimately inactivate the virus (causing G→A hypermutation, as readout on the genomic strand of the virus). APOBEC3F is a homolog of APOBEC3G and restricts HIV-1 infection by a similar mechanism. APOBEC3F and -3G deaminate cytosines within different local contexts, preferring 5'-TC and 5'-CC, respectively.

The nucleic acid sequence encoding the cytosine deaminase can be a cDNA or can include introns or adjacent 5'- or 3'-untranslated regions (e.g., a genomic nucleic acid). For example, the nucleic acid sequence can encode a human APOBEC3F or APOBEC3G polypeptide. GenBank Accession Nos. NM_145298 and NM_021822 provide the sequences of the human APOBEC3F and APOBEC3G cDNAs, respectively. The nucleic acid sequence also can encode a sheep or cow APOBEC3F polypeptide as described herein. The sheep and cow APOBEC3F proteins have an active amino terminal DNA cytosine deaminase domain, which elicits a broader dinucleotide deamination preference, and are fully resistant to HIV-1 Vif.

Nucleic acid sequences having silent mutations that do not change the encoded amino acids or sequence variants that do change one or more encoded amino acids, but do not abolish enzymatic function, also can be used. For example, the nucleic acid sequence of the APOBEC3G used herein differs from the coding sequence of NM_021822 by a C to T transition at nucleotide position 588. This transition is silent and does not change the encoded amino acid at position 119 (F). In some embodiments, two or more cytosine deaminase polypeptides (e.g., the human APOBEC3F and APOBEC3G polypeptides) are encoded on the nucleic acid construct.

Nucleic Acid Constructs

Nucleic acid constructs of the invention include a nucleic acid sequence encoding a non-porcine cytosine deaminase. As used herein, the term "nucleic acid" includes DNA, RNA, and nucleic acid analogs, and nucleic acids that are double-stranded or single-stranded (i.e., a sense or an antisense single strand). Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, Summerton and Weller (1997) *Antisense Nucleic Acid Drug Dev.* 7(3):187-195; and Hyrup et al. (1996) *Bioorgan. Med. Chem.* 4(1):5-23. In addition, the deoxyphosphate backbone can be replaced with, for example, a phosphorothioate or phosphorodithioate backbone, a phosphoroamidite, or an alkyl phosphotriester backbone.

The nucleic acid sequence encoding the cytosine deaminase can be operably linked to a regulatory region such as a promoter. Regulatory regions can be porcine regulatory regions or can be from other species. As used herein, "operably linked" refers to positioning of a regulatory region relative to a nucleic acid sequence encoding a polypeptide in such a way as to permit or facilitate expression of the encoded polypeptide.

Any type of promoter can be operably linked to a nucleic acid sequence encoding a cytosine deaminase. Examples of promoters include, without limitation, tissue-specific promoters, constitutive promoters, and promoters responsive or unresponsive to a particular stimulus. Suitable tissue specific promoters can result in preferential expression of a nucleic acid transcript in islet cells and include, for example, the human insulin promoter. Other tissue specific promoters can result in preferential expression in, for example, hepatocytes or heart tissue and can include the albumin or alpha-myosin heavy chain promoters, respectively.

In other embodiments, a promoter that facilitates the expression of a nucleic acid molecule without significant tissue- or temporal-specificity can be used (i.e., a constitutive promoter). For example, a θ-actin promoter such as the chicken θ-actin gene promoter, ubiquitin promoter, glyceraldehyde-3-phosphate dehydrogenase (GAPDH) promoter, or 3-phosphoglycerate kinase (PGK) promoter can be used, as well as viral promoters such as the herpes virus thymidine kinase (TK) promoter, the SV40 promoter, or a cytomegalovirus (CMV) promoter. In some embodiments, a fusion of the chicken actin gene promoter and the CMV enhancer is used as a promoter. See, for example, Xu et al. (2001) *Hum. Gene Ther.* 12(5):563-73; and Kiwaki et al. (1996) *Hum. Gene Ther.* 7(7):821-30.

An example of an inducible promoter is the tetracycline (tet)-on promoter system, which can be used to regulate transcription of the nucleic acid. In this system, a mutated Tet repressor (TetR) is fused to the activation domain of herpes simplex VP 16 (transactivator protein) to create a tetracycline-controlled transcriptional activator (tTA), which is regulated by tet or doxycycline (dox). In the absence of antibiotic, transcription is minimal, while in the presence of tet or dox, transcription is induced. Alternative inducible systems include the ecdysone or rapamycin systems. Ecdysone is an insect molting hormone whose production is controlled by a heterodimer of the ecdysone receptor and the product of the ultraspiracle gene (USP). Expression is induced by treatment with ecdysone or an analog of ecdysone such as muristerone A.

Additional regulatory regions that may be useful in nucleic acid constructs, include, but are not limited to, polyadenylation sequences, translation control sequences (e.g., an internal ribosome entry segment, IRES), enhancers, inducible elements, or introns. Such regulatory regions may not be necessary, although they may increase expression by affecting transcription, stability of the mRNA, translational efficiency, or the like. Such regulatory regions can be included in a nucleic acid construct as desired to obtain optimal expression of the nucleic acids in the cell(s). Sufficient expression, however, can sometimes be obtained without such additional elements.

Other elements that can be included on a nucleic acid construct encode signal peptides or selectable markers. Signal peptides can be used such that the encoded polypeptide is directed to a particular cellular location (e.g., the cell surface). Non-limiting examples of selectable markers include puromycin, adenosine deaminase (ADA), aminoglycoside phosphotransferase (neo, G418, APH), dihydrofolate reductase (DHFR), hygromycin-B-phosphotransferase, thymidine kinase (TK), and xanthin-guanine phosphoribosyl-transferase (XGPRT). Such markers are useful for selecting stable transformants in culture.

In some embodiments, a nucleic acid sequence encoding a cytosine deaminase can include a tag sequence that encodes a "tag" designed to facilitate subsequent manipulation of the encoded polypeptide (e.g., to facilitate localization or detection). Tag sequences can be inserted in the nucleic acid sequence encoding the cytosine deaminase polypeptide such that the encoded tag is located at either the carboxyl or amino terminus of the cytosine deaminase polypeptide. Non-limiting examples of encoded tags include green fluorescent protein (GFP), glutathione S-transferase (GST), and Flag™ tag (Kodak, New Haven, Conn.).

Nucleic acid constructs can be introduced into embryonic, fetal, or adult porcine cells of any type, including, for example, germ cells such as an oocyte or an egg, a progenitor cell, an adult or embryonic stem cell, a kidney cell such as a PK-15 cell, an islet cell, a θ cell, a liver cell, or a fibroblast such as a dermal fibroblast, using a variety of techniques. Non-limiting examples of techniques include the use of transposon systems, recombinant viruses that can infect cells, or liposomes or other non-viral methods such as electroporation, microinjection, or calcium phosphate precipitation, that are capable of delivering nucleic acids to cells.

In transposon systems, the transcriptional unit of a nucleic acid construct, i.e., the regulatory region operably linked to a nucleic acid sequence encoding a cytosine deaminase polypeptide, is flanked by an inverted repeat of a transposon. Several transposon systems, including, for example, Sleeping Beauty (see, U.S. Pat. No. 6,613,752 and U.S. Patent Publication No. 20050003542), Frog Prince (Miskey et al. (2003) *Nucleic Acids Res.* 31(23):6873-81), and Skipper have been developed to introduce nucleic acids into cells, including mice, human, and pig cells. The Sleeping Beauty transposon is particularly useful. A transposase can be encoded on the same nucleic acid construct or can be introduced on a separate nucleic acid construct.

Insulator elements also can be included in a nucleic acid construct to maintain expression of the cytosine deaminase polypeptide and to inhibit the unwanted transcription of host genes. See, for example, U.S. Patent Publication No. 20040203158. Typically, an insulator element flanks each side of the transcriptional unit and is internal to the inverted repeat of the transposon. Non-limiting examples of insulator elements include the matrix attachment region (MAR) type insulator elements and border-type insulator elements. See, for example, U.S. Pat. Nos. 6,395,549, 5,731,178, 6,100,448, and 5,610,053, and U.S. Patent Publication No. 20040203158.

Viral vectors that can be used include adenovirus, adeno-associated virus (AAV), retroviruses, lentiviruses, vaccinia virus, measles viruses, herpes viruses, and bovine papilloma virus vectors. See, Kay et al. (1997) *Proc. Natl. Acad. Sci. USA* 94, 12744-12746 for a review of viral and non-viral vectors. Viral vectors are modified so the native tropism and pathogenicity of the virus has been altered or removed. The genome of a virus also can be modified to increase its infectivity and to accommodate packaging of the nucleic acid encoding the polypeptide of interest.

Adenoviral vectors can be easily manipulated in the laboratory, can efficiently transduce dividing and nondividing cells, and rarely integrate into the host genome. Smith et al. (1993) *Nat. Genet.* 5, 397-402; and Spector and Samaniego (1995) *Meth. Mol. Genet.*, 7, 31-44. The adenovirus can be modified such that the E1 region is removed from the double stranded DNA genome to provide space for the nucleic acid encoding the polypeptide and to remove the transactivating E1a protein such that the virus cannot replicate. Adenoviruses have been used to transduce a variety of cell types, including, inter alia, keratinocytes, hepatocytes, and epithelial cells.

Adeno-associated viral (AAV) vectors demonstrate a broad range of tropism and infectivity, although they exhibit no human pathogenicity and do not elicit an inflammatory response. AAV vectors exhibit site-specific integration and can infect non-dividing cells. AAV vectors have been used to deliver nucleic acid to brain, skeletal muscle, and liver over a long period of time (e.g., >9 months in mice) in animals. See, for example, U.S. Pat. No. 5,139,941 for a description of AAV vectors.

Retroviruses are the most-characterized viral delivery system and have been used in clinical trials. Retroviral vectors mediate high nucleic acid transfer efficiency and expression. Retroviruses enter a cell by direct fusion to the plasma membrane and integrate into the host chromosome during cell division.

Lentiviruses also can be used to deliver nucleic acids to cells, and in particular, to non-dividing cells. Replication deficient HIV type I based vectors have been used to transduce a variety of cell types, including stem cells. See, Uchidda et al. (1998) *Proc. Natl. Acad. Sci. USA* 95, 11939-11944.

Non-viral vectors can be delivered to cells via liposomes, which are artificial membrane vesicles. The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Transduction efficiency of liposomes can be increased by using dioleoylphosphatidylethanolamine during transduction. See, Felgner et al. (1994) *J. Biol. Chem.* 269, 2550-2561. High efficiency liposomes are commercially available. See, for example, SuperFect® from Qiagen (Valencia, Calif.).

Transgenic Pigs

The nucleated cells of the transgenic pigs provided herein contain a nucleic acid construct described above. As used herein, "transgenic pig" includes founder transgenic pigs as well as progeny of the founders, progeny of the progeny, and so forth, provided that the progeny retain the nucleic acid construct. For example, a transgenic founder animal can be used to breed additional animals that contain the nucleic acid construct.

Tissues obtained from the transgenic pigs and cells derived from the transgenic pigs also are provided herein. As used herein, "derived from" indicates that the cells can be isolated directly from the pig or can be progeny of such cells. For example, brain, lung, liver, pancreas, heart and heart valves, muscle, kidney, thyroid, corneal, skin, blood vessels or other connective tissue can be obtained from a pig. Blood and hematopoietic cells, Islets of Langerhans, θ cells, brain cells, hepatocytes, kidney cells, and cells from other organs and body fluids, for example, also can be derived from transgenic pigs. Organs and cells from transgenic pigs can be transplanted into a human patient. For example, islets from transgenic pigs can be transplanted to human diabetic patients.

Various techniques known in the art can be used to introduce nucleic acid constructs into non-human animals to produce founder lines, in which the nucleic acid construct is integrated into the genome. Such techniques include, without limitation, pronuclear microinjection (U.S. Pat. No. 4,873,191), retrovirus mediated gene transfer into germ lines (Van der Putten et al. (1985) *Proc. Natl. Acad. Sci. USA* 82, 6148-1652), gene targeting into embryonic stem cells (Thompson et al. (1989) *Cell* 56, 313-321), electroporation of embryos (Lo (1983) *Mol. Cell. Biol.* 3, 1803-1814), and in vitro transformation of somatic cells, such as cumulus or mammary cells, or adult, fetal, or embryonic stem cells, followed by nuclear transplantation (Wilmut et al. (1997) *Nature* 385, 810-813; and Wakayama et al. (1998) Nature 394, 369-374). Pronuclear microinjection and somatic cell nuclear transfer are particularly useful techniques.

Typically, in pronuclear microinjection, a nucleic acid construct described above is introduced into a fertilized egg; 1 or 2 cell fertilized eggs are used as the pronuclei containing the genetic material from the sperm head and the egg are visible within the protoplasm. Linearized nucleic acid constructs can be injected into one of the pronuclei then the injected eggs can be transferred to a recipient female (e.g., into the oviducts of a recipient female) and allowed to develop in the recipient female to produce the transgenic pigs.

In somatic cell nuclear transfer, a transgenic pig cell such as a fetal fibroblast that includes a nucleic acid construct described above, can be introduced into an enucleated oocyte to establish a combined cell. Oocytes can be enucleated by partial zona dissection near the polar body and then pressing out cytoplasm at the dissection area. Typically, an injection pipette with a sharp beveled tip is used to inject the transgenic cell into an enucleated oocyte arrested at meiosis 2. In some conventions, oocytes arrested at meiosis 2 are termed "eggs." After producing a porcine embryo (e.g., by fusing and activating the oocyte), the porcine embryo is transferred to the oviducts of a recipient female, about 20 to 24 hours after activation. See, for example, Cibelli et al. (1998) *Science* 280, 1256-1258 and U.S. Pat. No. 6,548,741.

Recipient females can be checked for pregnancy approximately 20-21 days after transfer of the embryos.

Standard breeding techniques can be used to create animals that are homozygous for the cytosine deaminase polypeptide from the initial heterozygous founder animals. Homozygosity may not be required, however, to observe a decreased capability of transmitting PERV to human cells.

Once transgenic pigs have been generated, expression of cytosine deaminase polypeptides can be assessed using standard techniques. Initial screening can be accomplished by Southern blot analysis to determine whether or not integration of the construct has taken place. For a description of Southern analysis, see sections 9.37-9.52 of Sambrook et al., 1989, *Molecular Cloning, A Laboratory Manual*, second edition, Cold Spring Harbor Press, Plainview; NY. Polymerase chain reaction (PCR) techniques also can be used in the initial screening PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. PCR is described in, for example *PCR Primer: A Laboratory Manual*, ed. Dieffenbach and Dveksler, Cold Spring Harbor Laboratory Press, 1995. Nucleic acids also can be amplified by ligase chain reaction, strand displacement amplification, self-sustained sequence replication, or nucleic acid sequence-based amplified. See, for example, Lewis (1992) *Genetic Engineering News* 12, 1; Guatelli et al. (1990) *Proc. Natl. Acad. Sci. USA* 87, 1874-1878; and Weiss (1991) *Science* 254, 1292-1293.

Expression of a nucleic acid sequence encoding a cytosine deaminase polypeptide (e.g., an APOBEC3F and/or APOBEC3G polypeptide) in the tissues of transgenic pigs can be assessed using techniques that include, without limitation, Northern blot analysis of tissue samples obtained from the animal, in situ hybridization analysis, Western analysis, immunoassays such as enzyme-linked immunosorbent assays, and reverse-transcriptase PCR (RT-PCR). Expression of a non-porcine cytosine deaminase polypeptide in at least some of the cells of the pig can result, upon co-culture with human cells, in a decreased capability of the cells to transmit PERV to the human cells.

Decreased capability to transmit PERV can be assessed, for example, by a co-culture assay. Transgenic pig cells and human cells (e.g., 293T cells) can be physically separated by a thin membrane with 1 micron-sized pores and co-cultured for approximately 50 generations or 25 days. Such a membrane permits free diffusion of small molecules including viral particles but does not permit diffusion of cells. At the end of the culturing period, the human cells can be harvested and tested for PERV reverse transcriptase activity (as a measure of infectivity) using an ELISA assay (e.g., from Cavidi Tech, Uppsala, Sweden). It is understood that a particular phenotype in a transgenic animal typically is assessed by comparing the phenotype in the transgenic animal to the corresponding phenotype exhibited by a control non-human animal that lacks the transgene.

Transgenic pigs of the invention can be bred with other animals of interest (e.g., animals with transplantation-compatible backgrounds such as pigs with an inactivated I-1,3 galactosyl transferase gene). The resulting progeny animals may be particularly useful for xenotransplantation due to the decreased risk of transmitting endogenous retroviruses to human cells and the decreased risk of hyperacute rejection. Such animals can be produced by, for example, crossing (a) a transgenic pig expressing a non-porcine cytosine deaminase polypeptide with (b) a transgenic pig with an inactivated I-1,3 galactosyl transferase gene. Alternatively, a single line of transgenic pigs can be produced by initially preparing the pigs using the appropriate transgenes.

The invention is further described in the following examples, which do not limit the scope of the invention described in the claims.

EXAMPLES

Example 1

Methods and Materials for Examples 2-7

Yeast Strains.

Yeast mutation assays were done in L40 (MATa his3-200 trp1-901 leu2-3112 ade2 LYS2::(lexAop)$_4$-HIS3 URA3:: (lexAop)$_8$-lacZ GAL4) (1). Retrotransposition assays were done in DG1251 (MATa ura3-167 trp1-hisG spt3-101 his3-200) or GRY1990, a derivative of DG1251 in which E. coli θ-galactosidase is constitutively expressed from the yeast PGK1 promoter (Nissley et al., (1996) Nature 380, 30; Nissley et al. (1998) Proc. Natl. Acad. Sci. USA 95, 13905-10). Endogenous retrotransposition assays were carried in DG1141 [MAT I trp1-hisG ura3-167 his3-200 Ty1-2y2his3AI; (Curcio and Garfinkel (1991) Proc. Natl. Acad. Sci. USA 88, 936-40). L40 ung1::kanMX4 was constructed by amplifying the ung1::kanMX4 cassette from yeast deletion strain 36067 (R. Wright, University of Minnesota), transforming L40 with the resulting PCR product and selecting G418-resistant colonies (Wach et al. (1994) Yeast 10, 1793-1808)). ung1 deletion was confirmed by PCR and screening for a modest CAN1mutator phenotype.

Plasmids.

Constructs were based on pHybLex-Zeo or pJG4-5 (Invitrogen, Carlsbad, Calif.). The LexAAPOBEC3G fusion protein was constructed by subcloning APOBEC3G from pAPOBEC3G-IRES-bleo (Harris et al. (2003) Cell 113, 803-809) using NotI and PstI. Untagged APOBEC3G in pHybLex-Zeo contains a 5 bp insertion between the LexA and APOBEC3G open reading frames.

Ugi was subcloned from pEF-Ugi (Di Noia and Neuberger (2002) Nature 419, 43-48) as an EcoRI and NotI fragment into pcDNA3.1 (Invitrogen). It was subcloned into pYES3-CT using HindIII and NotI (Invitrogen). Ugi expression was confirmed using the CAN1 mutation assay. The wild-type HIV-1 Vif sequences were amplified by PCR from HIV-1 YU-2 and IIIB proviral plasmids (M. Malim, Kings College London), digested with NcoI and BamHI and were first cloned into similarly cut pTrc99A (AP Biotech). Vif was subsequently subcloned into pHybLex-Zeo using a NcoI and PstI digest and finally into pJG4-5 using EcoRI and SphI. APOBEC3F was subcloned from pTrc99A-APOBEC3F (Liddament et al. (2004) Curr. Biol. 14, 1385-1391) into both pHybLex-Zeo and pJG4-5 using EcoRI and SalI.

Galactose(GAL)-inducible his3AI marked versions of Ty1 (pGALTy1) and TyHRT (pHART21) were described previously (Nissley et al., 1996, supra; Nissley et al., 1998, supra).

Yeast Mutation Assays.

pHybLex-Zeo, pJG4-5, pYES3-CT and their derivatives were transformed into L40 and selected using a synthetic complete medium containing zeocin (300 Tg/mL) and lacking tryptophan (SC+ZEO-TRP) (Ausubel et al. (2002) (John Wiley and Sons, Inc.). Several thousand viable cells from independent colonies were used to inoculate 2.5 ml SC+GAL+RAF+ZEO-TRP (2% galactose, 1% raffinose, 300 Tg/mL zeocin). Cultures were grown at 30° C. for 3-4 days, concentrated 5-fold and a fraction was plated to SC+CAN-ARG (30 Tg/mL CAN) to obtain canavanine resistant (Can$^R$) mutants. Viable cell counts were obtained by plating a dilution to rich medium. Viable cells were counted after 2 days and Can$^R$ colonies were counted after 3-4 days of incubation at 30° C. The CAN1 gene of Can$^R$ colonies was amplified by PCR and sequenced as previously reported (Marsischky et al. (1996) Gene Dev. 10, 407-420). Accurate values for the mutation frequencies were obtained by using multiple independent cultures (6-8) for each strain in each experiment and by repeating each experiment at least twice and as many as seven times. Sequencher (Genes Codes Corp) was used for mutational analyses.

Immunoblotting.

Cell pellets from a 10 mL log phase culture were washed with 1 mL 20% trichloroacetic acid (TCA), resuspended in 50 TL 20% TCA, and then lysed by vortexing with an equal volume of glass beads at 4° C. The supernatant was centrifuged to pellet the proteins. Pelleted proteins were resuspended in 100 TL SDS-gel loading buffer, separated by SDS-PAGE, transferred to a PVDF membrane and probed with antibodies to APOBEC3G (Newman et al. (2005) Curr. Biol. 15, 166-170), LexA (Invitrogen), or Vif (Fouchier et al (1996) J. Virol. 70, 8263-8269; Simon et al. (1997) J. Virol. 69, 4166-4172; Simon et al. (1997) J. Virol. 71, 5259-5267).

Ty1 Retrotransposition Assays.

Ty-his3AI, TyHRT-his3AI, Ty-lucAI or TyHRT-lucAI plasmids were co-transformed with pJG4-5, pJG4-5-APOBEC3G or pJG4-5-APOBEC3F into DG1251 or GRY1990 (Gietz et al. (1995) Yeast 11, 355-360) and selected using SC-URA-TRP+GLC.

his3AI transformants were grown in SC-URA-TRP+GLC to saturation. Approximately 10$^6$ cells were subcultured in 1 ml of SC-URA-TRP+GAL for 12 hrs and an aliquot was plated to SC-HIS. Cell viability was determined by plating a dilution to rich medium. Retrotransposition was quantified by determining the frequency of His+ colonies.

lucAI transformants were grown 1 day in SC-URA-TRP+ GLC. Cells were transferred to SC-URA-TRP+GAL and grown for an additional 2 days at 30° C. to induce retroelement expression and reverse transcription. Retrotransposition was quantified by measuring the relative active levels of luciferase to θ-galactosidase. All incubations for plasmid-based Ty1 assays were at 30° C.

For endogenous retrotransposition assays, DG1141 was transformed with pJG4-5, pJG4-5-APOBEC3G, or pJG4-5-APOBEC3F. Single colonies were resuspended in water and 10-50,000 cells were transferred to 2 mL SC-TRP+GAL and grown at 20° C. for 7-10 days until the cultures reached saturation. Dilutions of the starting and ending cultures were plated to rich media to determine the number of viable cells and the equivalent of 1 mL of the saturated culture was plated to SC-HIS to score retrotransposition events.

Ty1 DNA Sequencing.

Retrotransposed Ty1 and TyHRT cDNAs were isolated by growing His$^+$ colonies overnight in 10 ml SC-HIS at 30° C. and preparing DNA with a standard glass bead/phenol extraction method. The resulting DNA was used to amplify a 1,026 (Ty) or 971 (TyHRT) by region spanning the RT gene and HIS3 using 5'-TTC ATG TGG GAC ACT AGA GAT (TyRT, SEQ ID NO:15) or 5'-CCT GAG TGG GAG TTG TTA (TyHRT, SEQ ID NO:2) and 5'-TAT GAT ACA TGC TCT GGC CAA (HIS3, SEQ ID NO:3). PCR products were purified (Qiagen) and sequenced with 5'-GT CTG CGA GGC AAG AAT GAT (SEQ ID NO:4). GFP-negative retrotransposition events were obtained from pools of His+ colony genomic DNA by transformation into E. coli. GFP-negative colonies were identified using fluorescent light and the resident plasmid DNA was amplified (as above except the product was 2.1 kb for Ty RT) and sequenced using 5'-C GTT ATC CGG ATC ATA TGA (SEQ ID NO:5) and 5'-G TAG TTC CCG TCA TCT TGA (SEQ ID NO:6).

Example 2

Figure 2:
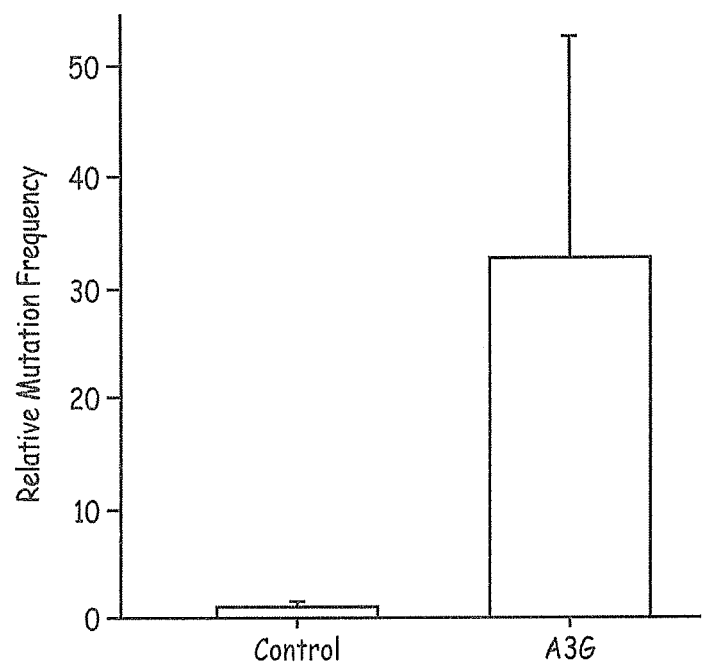
FIG. 2 reports the mean of the median values for these experiments). (B) APOBEC3G and Ugi co-expression triggers a synergistic increase in the frequency of mutation to CanI. APOBEC3G is tagged with the DNA binding domain of LexA unless noted. The parameters are identical to FIG. 1A.

APOBEC3G Stimulates Mutation in Saccharomyces cerevisiae Via the Uracil Excision Pathway To test whether human APOBEC3G could elicit its hallmark mutator activity in yeast, a LexA-APOBEC3G fusion protein was expressed in the haploid strain L40 and the accumulation of mutations that conferred resistance to the toxic amino acid canavanine was monitored. Liquid cultures were grown from individual colonies expressing APOBEC3G or a control vector and then plated onto a solid medium containing canavanine. The numbers of canavanine-resistant ($Can^R$) colonies were determined after 3-4 days growth. In contrast to cells expressing a control vector, those expressing LexAAPOBEC3G showed a 20-fold increase in the median frequency of $Can^R$ mutation, suggesting that APOBEC3G was capable of deaminating cytosines within yeast genomic DNA (FIG. 1A; FIG. 2).

To begin to determine whether the LexA-APOBEC3G-induced mutator phenotype occurred by a C→U deamination mechanism, it was asked whether a uracil DNA glycosylase deficiency would exacerbate this phenotype. Since most DNA-based organisms use uracil DNA glycosylase to rid their genomes of uracil (Barnes and Lindahl (2004) Annu. Rev. Genet. 38, 445-476), it was likely that if this were the mechanism then many of the APOBEC3G-induced uracil lesions would have been repaired and that the observed mutation frequency would be an underestimate of APOBEC3G activity. Indeed, yeast expressing both APOBEC3G and a uracil DNA glycosylase inhibitor (Ugi) protein showed a 320-fold increase in the median frequency of mutation to CanR (FIG. 1B). This stimulation was approximately 6-fold and 26-fold higher than that observed in LexA-APOBEC3G-expressing and in Ugi-expressing yeast cells, respectively, indicating that many of the APOBEC3G-dependent uracils were repaired by a uracil excision mechanism.

Figure 3:
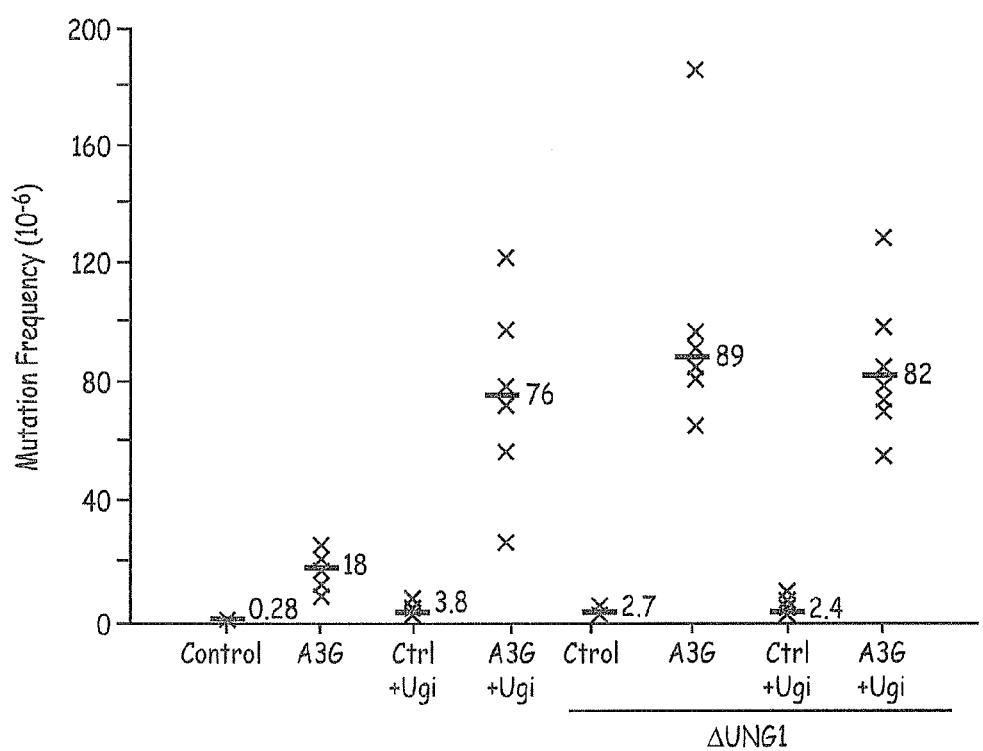
FIG. 3 is a histogram indicating that APOBEC3G stimulates mutation in S. cerevisiae by the uracil excision pathway II. Uracil DNA glycosylase inhibition by Ugi or its ablation by a deletion caused virtually identical phenotypes. The experimental parameters are identical to those described for FIG. 1A.

In yeast, the major uracil DNA glycosylase is Ung1p (uracil DNA N-glycosylase 1 protein). Ung1p and most other Ung proteins from bacteria to humans are strongly inhibited by Ugi (Mol et al., (1995) Cell 82, 701-708). However, Ugi-resistant uracil excision activities occur in mammalian cells, such as those elicited by the SMUG1 and TDG1 proteins (Barnes and Lindahl (2004) supra). To eliminate the possibility that some of the APOBEC3G-induced uracils might be repaired by auxiliary systems in yeast, homologous recombination was used to construct an Ung1p deletion strain, L40 ung1::kanMX4. This strain showed levels of $Can^R$ mutation virtually indistinguishable from Ugi-expressing cells in the presence or absence of APOBEC3G (FIG. 3). Thus, the majority of APOBEC3G-induced lesions in yeast were repaired by an Ung1p-dependent mechanism. Together with the exquisite specificity that Ung1p has for uracil, these data indicated that the APOBEC3G-dependent mutator phenotype was attributable to a DNA cytosine deamination mechanism.

APOBEC3G is localized predominantly to the cytoplasm of mammalian cells. Therefore, it was surprising that its expression in yeast caused high mutation frequencies. To ensure that the high mutation frequencies were not attributable to the DNA binding properties of the LexA tag, the CAN1 mutation frequency was monitored of cells expressing either LexA-APOBEC3G or untagged APOBEC3G. Little difference in the overall median frequencies of $Can^R$ mutation was observed demonstrating that the DNA binding domain of LexA was not responsible for the APOBEC3G-dependent mutator phenotype (FIG. 1B).

Example 3

APOBEC3G Triggers Predominantly C/G→T/A Transition Mutations in Yeast

CAN1 encodes a membrane-spanning arginine transporter that must be inactivated for growth to occur in the presence of the toxic arginine analog canavanine. A wide variety of base substitution, insertion, deletion and more complex mutations can confer CanR [e.g., (Huang et al., (2003) Proc. Natl. Acad. Sci. USA 100, 11529-11534; Rattray et al (2002) Genetics 162, 1063-1077]. To further investigate the mechanism of the APOBEC3G-induced mutator phenotype, the CAN1 gene of a large number of CanR colonies was sequenced. In agreement with previous studies, cells containing a control vector displayed a wide range of CAN1 mutations including transitions (26%), transversions (43%), insertions (3%) and deletions (28%) (FIG. 4A-4B). In contrast, the vast majority (90%) of the CAN1 mutations in APOBEC3G expressing cells were C/G→T/A transitions. APOBEC3G induced transitions occurred at the expense of other types of mutations, accounting for the elevated $Can^R$ mutation frequency (FIG. 4A-4B).

Yeast lacking Ung1p due to Ugi expression also displayed an increased level of C/G→T/A transition mutations (64%), as would be expected of cells lacking uracil excision repair (FIG. 4C-4D). However, 5/7 of these transitions occurred at positions that were not mutated in APOBEC3G expressing cells. Co-expression of Ugi and APOBEC3G resulted in an even stronger C/G→T/A transition bias (95%), and 19/21 of these mutations occurred at sites that were also mutated in APOBEC3G expressing (Ugi negative) yeast cells (FIG. 4C-4D). These data further demonstrated that APOBEC3G is capable of triggering genomic hypermutation in yeast by a C→U deamination mechanism.

Example 4

Figure 4:
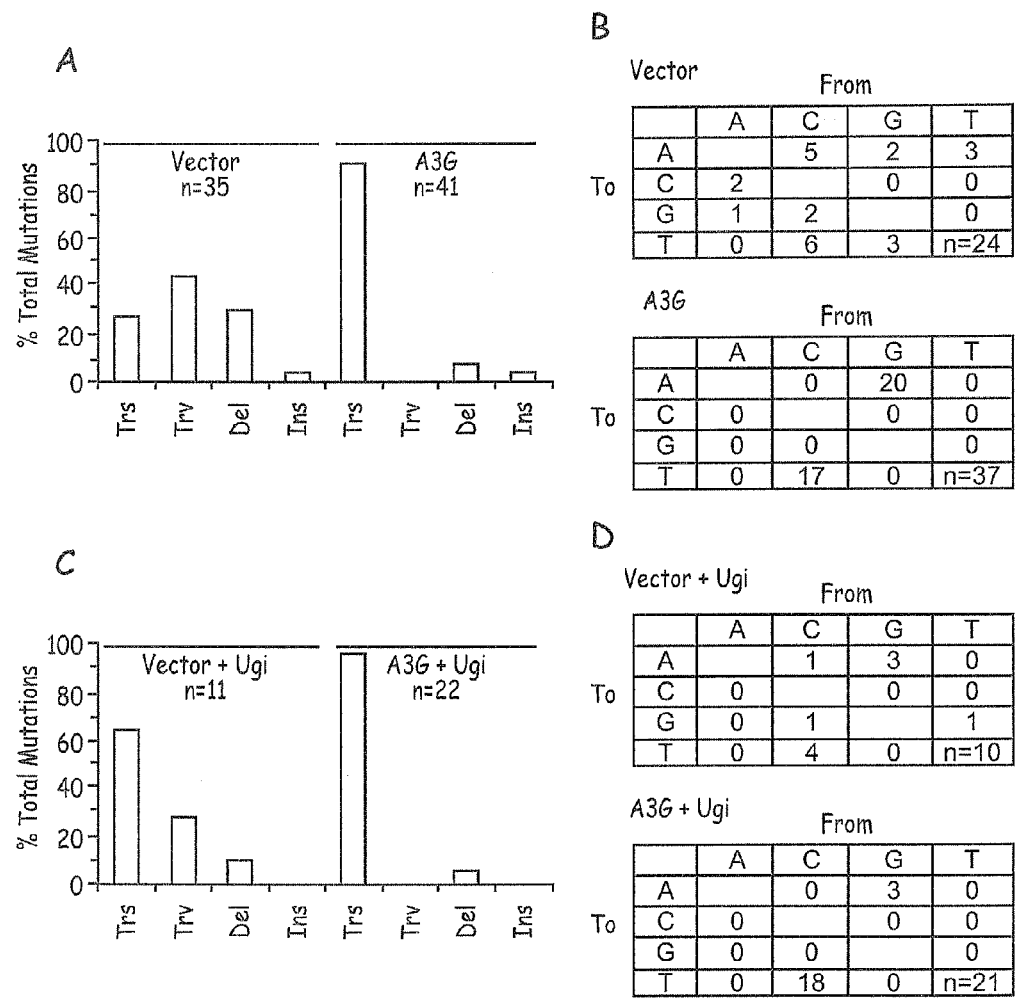
FIG. 4A-4D demonstrate that APOBEC3G triggers C/G→T/A transition mutations in S. cerevisiae. (A) Histograms summarizing the types of mutations found in the CAN1 gene of S. cerevisiae expressing a control vector or APOBEC3G. Data from Lex-APOBEC3G and untagged APOBEC3G expressing cells were nearly identical and were pooled for these analyses. Mutations were categorized as transitions (Trs), transversions (Try), deletions (Del) or insertions (Ins). (B) Summary of the base substitution mutations found in the CAN1 gene of S. cerevisiae expressing a control vector or APOBEC3G. (C) Histograms summarizing the types of mutations found in the CAN1 gene of S. cerevisiae expressing Ugi and a control vector or APOBEC3G. Labeled as in FIG. 4A. (D) Summary of the base substitution mutations found in the CAN1 gene of S. cerevisiae expressing Ugi and a control vector or APOBEC3G.
Figure 5:
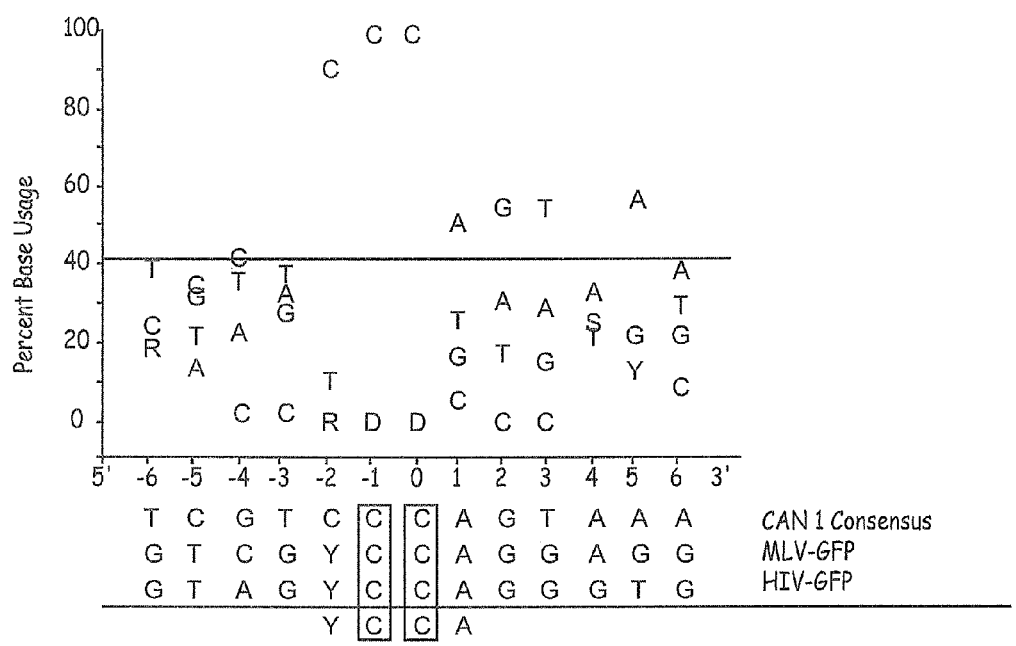
FIG. 5 is a graph illustrating the percentage that each base was found at the indicated position relative to the C/G→T/A transition mutation site in APOBEC3G expressing cells (n=37). The base found most frequently is indicated below. APOBEC3G consensus sites observed in model retroviral substrates, HIV-GFP or MLV-GFP, are shown (Liddament et al. (2004) Curr. Biol. 14, 1385-91). Multiple bases had the same percentage and are indicated by the one letter code where D=A/G/T, R=A/G, S=G/C and Y=C/T. The G/C content of the CANT gene is indicated by the dashed line. Can1 Consensus is SEQ ID NO:21, MLV-GFP is SEQ ID NO:22, and HIV-GFP is SEQ ID NO:23.

The Local APOBEC3G Mutation Preference in Yeast is Nearly Identical to that Observed in Model Retroviral Substrates A closer examination of the C/G→T/A transitions triggered by APOBEC3G expression revealed that 37/37 occurred within the dinucleotide 5'-CC, which could be found on either strand of the DNA duplex (FIGS. 4 and 5). APOBEC3G expression alone triggered C/G→T/A transition mutations at 14 distinct sites within the CAN1 gene. Co-expression of APOBEC3G and Ugi caused C/G→T/A transition mutations at 6 identical and 2 additional sites. The three most frequently APOBEC3G mutated 5'-CC dinucleotide sites, $C_{356}$, $C_{656}$, and $C_{1195}$, accounted for 48% of the total combined APOBEC3G- and APOBEC3G-plus-Ugidependent base substitution mutations. The extended sequence preference of APOBEC3G in the yeast system was compared to that defined previously in model HIV and MLV retroviral systems as 5'-YCCA [Y=C or T]. Interestingly, APOBEC3G exhibited a strikingly similar 5'-CCCA preference in yeast (FIG. 5), indicating that its preference as observed in other systems was intact.

It is further notable that in addition to a large number of C/G→T/A transition mutations, four deletions and a single insertion were detected in the CAN1 gene of APOBEC3G-expressing yeast cells (FIG. 4; combined data including the Ugi experiments). Three of five of these alterations occurred either in or immediately adjacent to a preferred or potential APOBEC3G hotspot, 5'-CCC. In contrast, only 1/12 of the deletions and insertions found in control vector containing cells occurred at similar sites. The remainder (11/12) were distributed throughout the CAN1 gene and were presumably caused by a variety of mechanisms. The presence of deletions and insertions associated with APOBEC3G hotspots suggested that C→U deamination events are able to precipitate gross genomic instability. This is further supported by our observation that a small (approximately 5%) proportion of $Can^R$ mutants failed to yield a CAN1 gene-specific PCR product, potentially representing larger-scale lesions.

Example 5

Affect of HIV-1 Vif on APOBE3G-Induced Yeast Hypermutation

In primates such as humans and chimpanzees, Vif counteracts the anti-retroviral activity of APOBEC3G by targeting it for proteasomal degradation. Vif accomplishes this by binding to APOBEC3G. Some data suggest that this association alone may directly impair APOBEC3G function (Stopak et al. (2003) *Mol. Cell.* 12, 591-601). Therefore, it was assessed whether the interaction between Vif and APOBEC3G could be detected using this yeast assay system.

HIV-1 Vif, derived from the YU2 or the IIIB provirus, was expressed alongside APOBEC3G using yeast two-hybrid bait or prey vectors. All possible pairwise combinations were tested for the ability to drive the yeast two-hybrid reporter genes lacZ or HIS3. No significant θ-galactosidase activity or histidine prototrophy was observed despite repeated attempts (data not shown). This result was not attributable to an expression failure as both proteins could be detected in cell lysates by immunoblotting.

However, because some weak or transient interactions may escape detection by the yeast two-hybrid assay, it was reasoned that the sensitive CAN1 mutation assay might provide a more robust method for monitoring this interaction. To examine whether HIV-1 Vif could affect APOBEC3G-mediated hypermutation in yeast, the $Can^R$ mutation frequencies of cells co-expressing Vif and APOBEC3G were compared with those of cells expressing either protein alone. The robust hypermutability of APOBEC3G was not significantly affected by HIV-1 Vif co-expression. Therefore, a Vif-APOBEC3G interaction in yeast was not detected.

Example 6

APOBEC3F and APOBEC3G Inhibit Ty1 Retrotransposition

Figure 6:
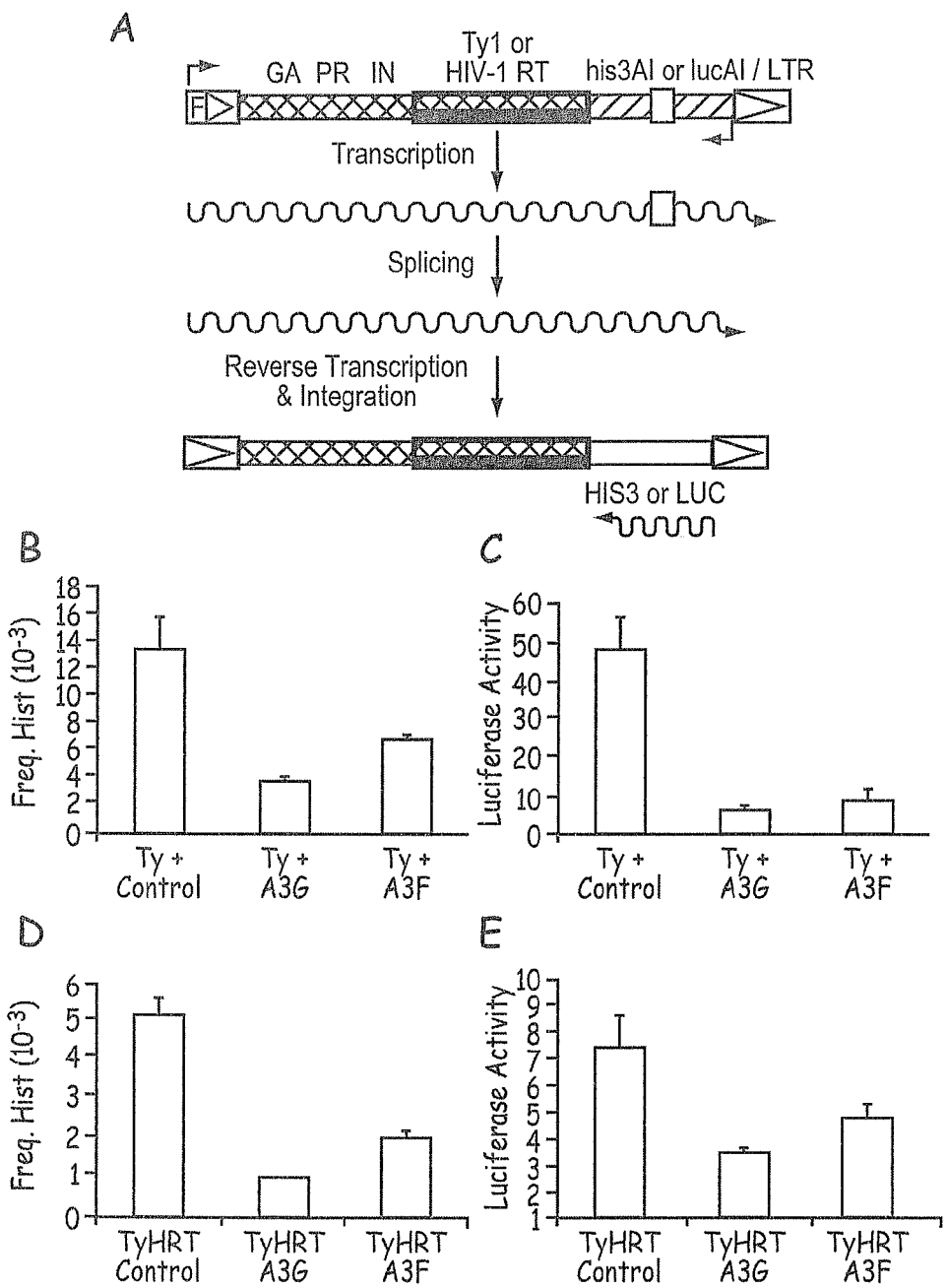
FIG. 6A-6D indicate that APOBEC3F and APOBEC3G inhibit Ty1 retrotransposition. (A) A schematic depicting retrotransposition by Ty1 or TyHRT yielding histidine prototrophy or luciferase activity. GA, PR, IN, RT and LTR represent gag, protease, integrase, reverse transcriptase and long-terminal repeat, respectively. (B, D) APOBEC3F or -3G expression diminishes Ty1 or TyHRT retrotransposition as monitored by the number of His+ colonies. For each condition, at least eight independent cultures were analyzed and the error bars depict one standard error of the mean. (C, E) APOBEC3F or -3G expression diminishes Ty1 or TyHRT retrotransposition as monitored by luciferase activity. The conditions were identical to those described above.

To explore the possibility that APOBEC3 proteins function to impede the mobility of endogenous retroelements that replicate using LTR sequences, the ability of the yeast retrotransposon Ty1 to replicate was assayed in the presence of APOBEC3G or its homolog APOBEC3F. Ty1 activity was monitored using an intron-disrupted retrotransposition indicator gene (FIG. 6A). Ty1 RNA expression, splicing, reverse transcription and integration yield functional reporter gene cDNA copies, encoding either histidine prototrophy or luciferase activity.

Figure 7:
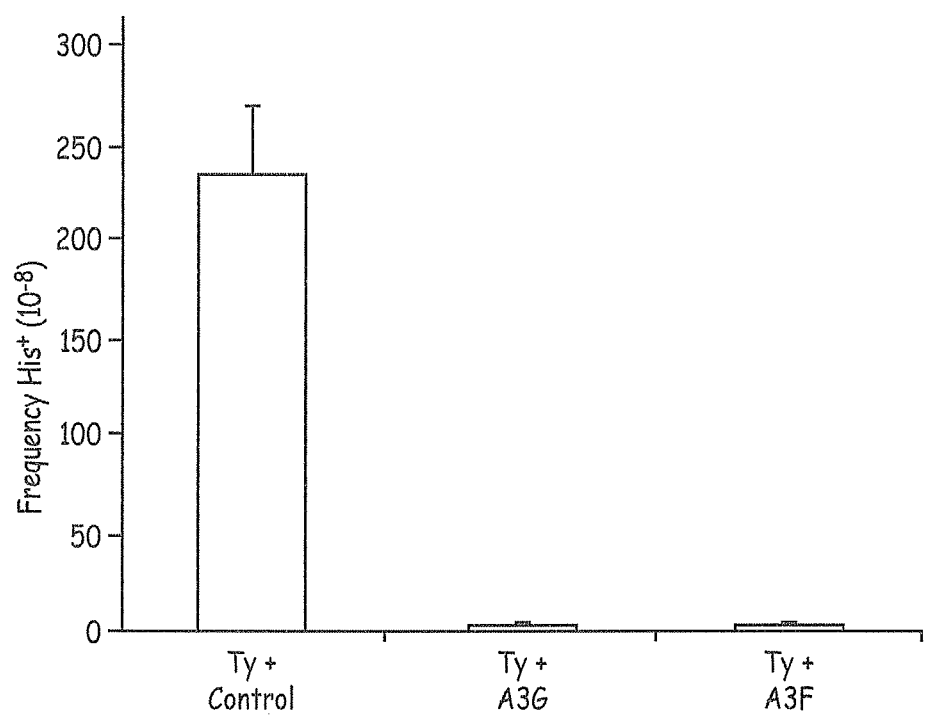
FIG. 7 is a graph of a representative experiment showing the effect of APOBEC3F or -3G expression on the retrotransposition of a chromosomal Ty1-his3AI element. APOBEC3F and -3G expression decreased the frequency of His+ retrotransposition by 94- and 98-fold, respectively. These effects were likely underestimates because several of the APOBEC3F and -3G expressing cultures failed to yield any His+ colonies (although viable cell counts indicated that they had grown to saturation). Note that the vector control level of His+ retrotransposition in this experiment is much lower than that shown in FIG. 6, because here the Ty1-his3AI construct is single-copy and its endogenous promoter is under cellular control the constructs used in FIG. 6 are expressed from multi-copy plasmids by a highly efficient GAL promoter]. The error bars indicate one SEM and they are barely visible for APOBEC3F and -3G.

The ability of Ty1-his3AI to retrotranspose was monitored in the presence of human APOBEC3F or -3G (FIG. 6B). In comparison to cells containing a control vector, an average of 51% or 70% fewer His$^+$ colonies were detected in the presence of APOBEC3F or -3G, respectively. Slightly larger APOBEC3-dependent declines in Ty1-lucAI retrotransposition were observed, as monitored by the relative levels of luciferase present in liquid cultures (FIG. 6C). However, an almost total inhibition (94-98%) was observed when retrotransposition of a genomic Ty1-his3AI element was assayed in the presence of APOBEC3F or -3G, suggesting that the ratio of APOBEC3 protein to retrotransposition intermediate (and/or Ty host factors) is a key determinant of this inhibitory mechanism (FIG. 7). Together, these data clearly demonstrated that APOBEC3F or -3G can inhibit Ty1 retrotransposition.

To assess whether the APOBEC3-dependent inhibition of retrotransposition in yeast could be influenced by the reverse transcriptase or the integration pathway, similar assays were performed with Ty1 constructs in which the normal reverse transcriptase was replaced with that from HIV-1 [TyHRT]. TyHRT integration occurs predominantly by homologous recombination, whereas Ty1 integration mostly uses its own integrase. Retrotransposition of both TyHRT-hisAI and TyHRT-lucAI (i.e., the accumulation of HIV-1 reverse transcriptase products) was also inhibited by APOBEC3F or APOBEC3G expression (FIGS. 6D, E). Levels of inhibition were roughly similar to those observed with Ty1 reverse transcriptase, indicating that neither the reverse transcriptase nor the integration pathway were key effectors of the APOBEC3-imposed retrotransposition block. These data further highlight the utility of the yeast Ty1 system for studying aspects of both APOBEC3 and HIV-1 biology.

Example 7

Ty1 Restriction by APOBEC3F and APOBEC3G Involves a cDNA Cytosine Deamination Mechanism As cDNA C→U deamination is a hallmark anti-retroviral activity of APOBEC3F and -3G, it was asked whether this could account for the observed Ty1 retrotransposition block. If so, it was expected that an inordinate number of retrotransposon minus strand C→T transition mutations would be found amongst the His$^+$ integrants (equivalent to plus strand G→A transitions). Over 26 and 47 kbp was sequenced of TyRT-HIS3 template generated in the presence of APOBEC3F and -3G, respectively, and only two C→T transitions were found among the APOBEC3G-exposed templates. One occurred within a dinucleotide consensus 5'-GC that is rarely preferred by this protein, and it therefore likely represents a reverse transcription or PCR error. The second occurred within the trinucleotide 5'-CCC, which is the most common APOBEC3 G preferred site. However, this meager number of base substitutions may have been in part due the fact that functional His$^+$ (and not His$^-$) integrants were analyzed. It is further possible that uracil residues within the retrotransposon cDNA triggered its degradation, as hypothesized originally for retroviruses (Harris et al. (2003) *Cell* 113, 803-809).

Therefore, to address the former possibility and to enrich for mutations, a modified version of the Ty-his3AI system was used in which a GFP cassette was placed upstream of his3AI (FIG. 8A). This enabled the selection of His+ integrants and a subsequent screen for unselected GFP-negative variants. Twenty independent GFP mutants were recovered from retrotransposition experiments in which APOBEC3G was expressed. Each sequence contained at least one mutation and as many as 15 mutations. In total, 57 base substitution mutations were identified and 47 of these were minus strand C→T transitions (FIG. 8B, FIG. 9A). Almost all of the APOBEC3G-dependent transitions occurred within the consensus 5'-YCC, identical to the preferred cytosine deamination consensus site in the CAN1 gene and in a variety of other systems (e.g., compare FIG. 9B and FIG. 5). Moreover, many of the C→T transitions occurred at positions that were identical to those observed previously in GFP-encoding HIV or MLV. A similar strand-specific transition bias and sequences with multiple transitions were found in GFP-negative templates produced in the presence of APOBEC3F (FIG. 9C; FIG. 8B). However, in contrast to APOBEC3G, the APOBEC3F-dependent mutations occurred within a distinct 5'-TTC consensus [FIG. 9D; observed previously with an HIV substrate]. Thus, Ty1 retrotransposition can be inhibited by APOBEC3F and -3G and much (and possibly all) of this effect can be attributed to a cDNA cytosine deamination mechanism.

Example 8

Expression of Human APOBEC3G in Pig Cells Reduces Transfer of Porcine Endogenous Retrovirus (PERV) to Human 293T Cells A construct for expression of human APOBEC3G was produced using the cytomegalovirus (CMV) promoter to drive expression and the neomycin gene as a selectable marker. To assess whether the APOBEC3G protein can inhibit PERV transmission to human cells, the construct was stably introduced into pig kidney PK-15 cells (ATCC # CCL-33) using Fugene® 6 reagent (Roche Applied Science, Indianapolis, Ind.) and cells were selected for neomycin resistance. PK-15 cells were chosen for these experiments because the PERVs residing in these cells were able to infect human 293T cells in simple supernatant mixing experiments (Patience et al., (1997) *Nat Med* 3, 282-286). (Note that PERVs can transmit as solution-soluble cell-free particles and/or through cell-cell contact). APOBEC3G expression in PK-15 cells was confirmed using specific antibodies (Newman et al. (2004) *Curr Biol.* 15(2):166-70).

Figure 10:
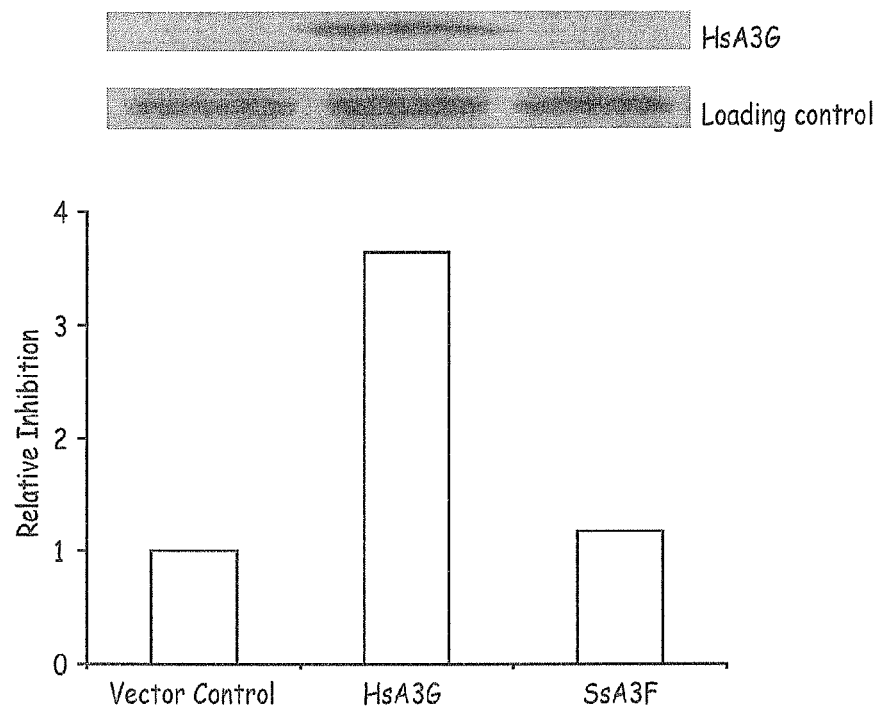
FIG. 10 is a graph indicating human APOBEC3G expression in pig kidney (PK-15) cells causes a 3-fold decline in PERV transfer to human 293T cells in a long-term co-culture experiment. The top two panels are immunoblots showing expression of human APOBEC3G (HsA3G) in PK-15 cells (center lane), but not in vector only or pig APOBEC3F (SsA3F) expressing cells (left and right lane, respectively). Non-specific bands are shown as loading controls.

PK-15 cells expressing a vector control, human APOBEC3G (hA3G), or pig APOBEC3F (SsA3F) were co-cultured with human 293T cells for 25 days (approximately 50 cell generations); the two cell types were physically separated by a thin membrane with 1 micron-sized pores, which permitted free diffusion of small molecules including viral particles but it did not permit diffusion of cells. After 25 days, whole cell protein extracts were prepared from the 293T cells using standard procedures. Cell lysates (10 Tg) were tested for PERV reverse transcriptase (RT) activity (as a measure of PERV transfer to the human cells) using the C-type retrovirus RT3 Activity ELISA assay; performed as recommended by the manufacturer, Cavidi Tech, Uppsala, Sweden. Little activity was detected in 293T cells grown in the presence of human APOBEC3G-expressing PK-15 cells, in contrast to controls where significant levels of infection were detected (FIG. 10). Results in FIG. 10 are shown as relative fold inhibition of RT activity normalized to RT activity in 293T cells cultured with PK-15 cells expressing an empty vector. This experiment indicates that expression of human A3G (but not expression of additional pig APOBEC3F) in PK-15 cells inhibits PERV transfer from PK-15 cells to 293T cells.

Figure 11:
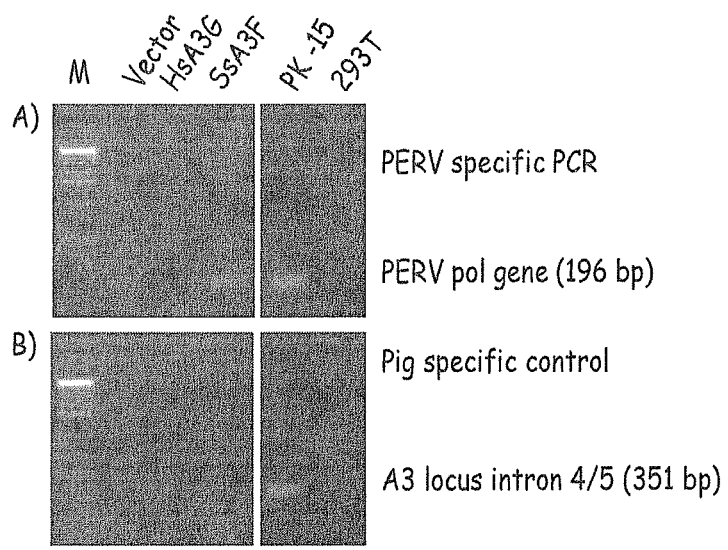
FIG. 11A is a picture of PCR products from a representative semi-quantitative PCR assay showing that human APOBEC3G potently diminishes PERV transfer from pig to human cells.
FIG. 11B is the pig specific control.

Semi-quantitative and quantitative, real-time PCR assays were performed to monitor for the presence of integrated PERV DNA in human 293T cells. Semi-quantitative PCR was performed using 75 ng of template genomic DNA from human 293T cells and primers (forward 5'-AA CCC TTT ACC CTT TAT GTG GAT-3', SEQ ID NO:16; reverse 5'-AA AGT CAA TTT GTC AGC GTC CTT-3', SEQ ID NO:17) made to the PERV pol gene (product size: 196 bp). As indicated in FIG. 11A, very little PERV DNA was detected in 293T cells grown in the presence of human APOBEC3G-expressing PK-15 cells, in contrast to other samples where significant levels were detected. To ensure that the human cell co-culturing compartment was not contaminated by pig cells (i.e., micro-chimerism), PCR also was performed using primers specific to pig DNA (forward 5'-GG AAC CTG CAA CCT ATG GAA-3', SEQ ID NO:18; reverse 5'-GG TGT GGC CCT AAA AAG ACA-3', SEQ ID NO:19) (351 bp product). The left panel of FIG. 11B shows that no pig PCR products were detected in 293T samples from the co-culture experiment. The right panel contains positive and negative controls. Micro-chimerism was not detected.

Figure 12:
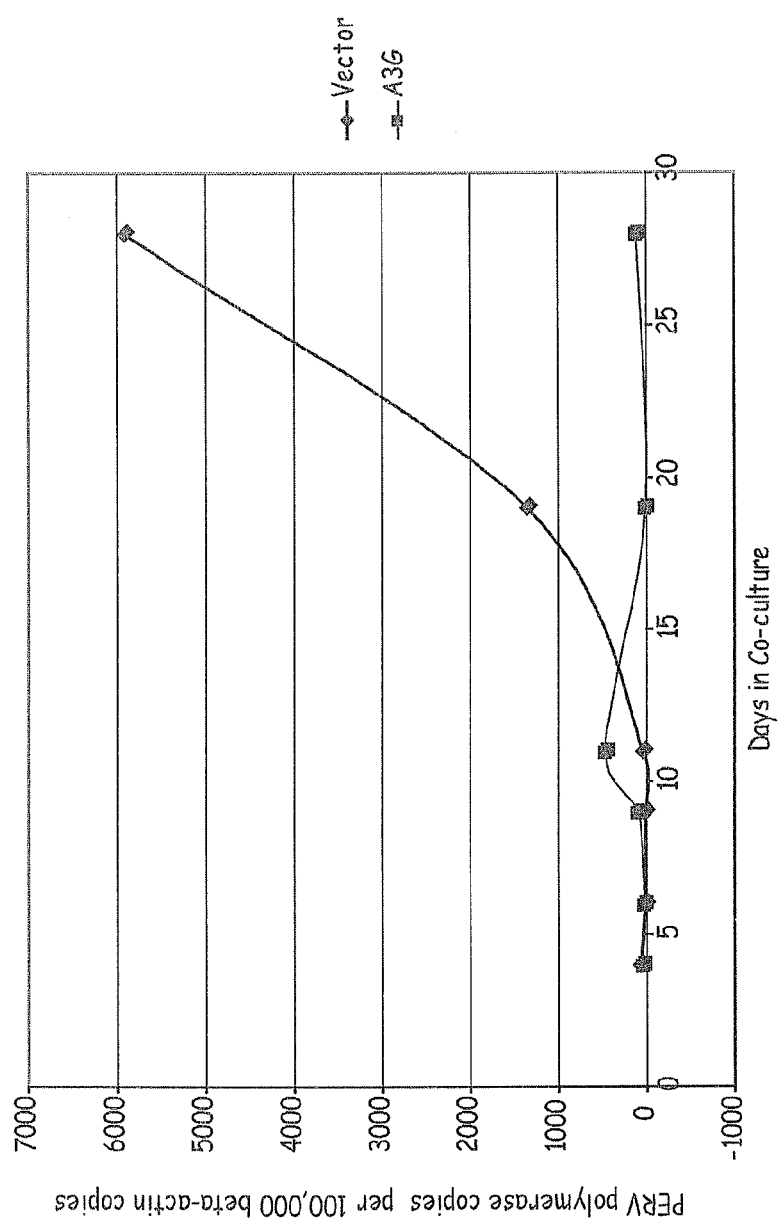
FIG. 12 is a graph from a representative quantitative, real-time PCR assay showing that human APOBEC3G potently diminishes PERV transfer from pig to human cells.

Quantitative, real-time PCR assays were performed in 25 TL reactions containing 10 ng of 293T genomic DNA, 100 nM primers, and 2× iQ SYBR Green super mix (BioRad, Hercules, Calif.) and run on an iCycler iQ Multicolor Real-Time PCR detection System (BioRad, Hercules, Calif.). Thermocycler conditions were 95° C. for 5 min followed by 50 cycles of 95° C. for 15 seconds and 60° C. for 30 seconds. A melting curve analysis directly followed the cycling to verify amplification of the PERV pol gene PCR product (amplified as discussed above). The human beta-actin gene (housekeeping gene) was amplified as an internal control using the following primers: Forward, 5'-AT CAT GTT TGA GAC CTT CAA-3' (SEQ ID NO:20) and reverse, 5'-A GAT GGG CAC AGT GTG GGT-3' (SEQ ID NO:7) (product size: ca. 100 bp). All data were normalized and PERV gene copies are presented per 100,000 beta-actin copies (FIG. 12). PERV transfer was apparent after 20 days of continuous co-culture in the vector control cells, whereas little transfer occurred in the presence of human APOBEC3G. Thus, expression of human APOBEC3G in pig PK-15 cells inhibited PERV transfer from pig PK-15 cells to human 293T cells.

Example 9

Artiodactyl Double Deaminase Domain APOBEC3F Proteins

NCBI BLAST searches were performed using the human and mouse A3 deaminase domains as query polypeptides. Several artiodactyl (cloven hoof ungulates) ESTs were identified, which suggested the presence of at least one A3 protein in cattle (*Bos taurus* (Bt), GenBank Accession No. BE684372, Smith et al, *Gen. Res.* 11(4): 626-630, 2001) and pigs (*Sus scrofa* (Ss), GenBank Accession No. BI346898, Fahrenkrug et al., 2002, *Mamm Genome,* 13, 475-478). Corresponding cDNA clones were obtained, sequenced and shown to encode A3 proteins with two putative zinc-binding, cytosine deaminase domains. The orthologous sheep (*Ovis aries*, Oa) double domain A3 cDNA sequence was obtained using a combination of degenerate PCR and nested 3' prime RACE. All three of these A3 proteins were similar in size to the 373 amino acid HsA3F protein, except the pig A3 protein, which was slightly longer due to a unique C-terminal, serine-rich extension. The cow, sheep, and pig A3 proteins are referred to herein as BtA3F (SEQ ID NO:8), OaA3F (SEQ ID NO:9) and SsA3F (SEQ ID NO:10), respectively. An alignment of the amino acid sequences of BtA3F, OaA3F, and SsA3F is shown in FIG. 13.

Amino acid alignments of the active deaminase domains (plus five residues on each side) were made using Clustal W software (Higgins et al. 1994, *Methods Mol Biol.* 25:307-18). The cow and sheep A3 active sites were 78% identical. Both the cow and the sheep proteins shared a lower level of identity with the pig protein (56%). The active sites of these artiodactyl A3 proteins were 56-62% identical to HsA3F (FIG. 14).

To test whether the artiodactyl A3F proteins have the capacity to deaminate cytosines within single-strand DNA, the intrinsic mutator activity of these proteins was monitored using an *E. coli* based mutation assay. Rifampicin resistance (RifR) is attributable to base substitution mutations in the *E. coli* RNA polymerase B (rpoB) gene, and it occurs in approximately one of every five million bacterial cells. This assay therefore provides a robust measure of intrinsic DNA cytosine deaminase activity. See, for example, Haché et al. (2005) *J Biol Chem,* 280, 10920-10924; Harris et al. (2002) *Molecular* Cell, 10, 1247-1253. Expression of each of the artiodactyl A3 proteins increased the RifR mutation frequency in *E. coli* from 3- to 7-fold, levels that were higher than those attributable to HsA3F but slightly lower than that those caused by HsA3G. BtA3F and SsA3F expression triggered a HsAID-like increase in RifR mutation frequency.

Artiodactyl A3F DNA cytosine deamination preferences were examined by sequencing the rpoB gene of at least 100 independent RifR mutants. In contrast to HsA3F and HsA3G, which preferentially deaminate cytosines at rpoB nucleotide positions 1721 and 1691, 5'-TC and 5'-CC, respectively, the artiodactyl A3F proteins showed less biased rpoB mutation spectra. OaA3F preferentially deaminated cytosine 1576, which is part of a 5'-GC dinucleotide. SsA3F also preferred cytosine 1576. However, SsA3F also clearly deaminated cytosine 1586, which is part of a 5'-AC dinucleotide. The main conclusion from the RifR mutation assays was that all three of the artiodactyls A3F proteins were capable of deaminating DNA cytosines and triggering a corresponding shift in the pattern of C/G→T/A transition mutations within the rpoB mutation substrate. Since the intrinsic DNA cytosine deamination preferences of HsA3F and HsA3G are apparent in retroviruses like HIV-1, these data suggest that the physiological dinucleotide substrates of OaA3F and SsA3F will be 5'-GC, and 5'-RC, respectively (R=A or G).

As an initial step toward understanding the potential retroelement targets of the artiodactyl A3F proteins, the sub-cellular distribution of these proteins was determined by live cell fluorescence microscopy. Approximately 7,500 HeLa cells were seeded on LabTek chambered coverglasses (Nunc). After 24 hrs of incubation, the cells were transfected with 200 ng of the pEGFP-A3-based DNA constructs. After an additional 24 hrs of incubation, images of the live cells were collected using a Zeiss Axiovert 200 microscope at 400× total magnification. In contrast to HsA3B and an eGFP control, which localized to the nucleus and the entire cell, respectively, the artiodactyl A3F proteins and MmA3 (mouse) were predominantly cytoplasmic, with punctate bodies apparent in some cells. This pattern of localization is identical to that seen for HsA3F and HsA3G, indicating that the artiodactyl A3F proteins might similarly function to inhibit the replication of LTR-dependent retroviruses such as HIV or MLV.

Example 10

Retrovirus Restriction by Artiodactyl A3F Proteins

It was tested whether the artiodactyl A3F proteins could inhibit the infectivity of HIV- and MLV-based retroviruses. In these systems, a GFP gene embedded in proviral DNA provides a measure of both transfection efficiency (which correlates directly with virus production levels) and of viral infectivity. 293T cells were grown in Dulbecco's modified Eagle's medium (Invitrogen) containing 10% fetal bovine serum (Gemini Bioproducts), penicillin, and streptomycin (Invitrogen). HIV-GFP [also called CS-CG] was produced by FuGENE® 6 (Roche Applied Sciences)-mediated transfection of 50-70% confluent 293T cells with a plasmid mixture containing 0.22 µg of CS-CG, 0.14 µg of pRK5/Pack1 (Gag-Pol), 0.07 µg of pRK5/Rev, 0.07 µg of pMDG (VSV-G Env), and 0.5 µg of an APOBEC expression or empty vector control plasmid as described previously (Liddament et al. (2004) *Curr Biol* 14:1385-1391). After an incubation period of 48 hr, virus-containing supernatants were clarified by low speed centrifugation, filtered (0.45 µm), and quantified using a reverse transcriptase activity based ELISA (Cavidi Tech). Reverse transcriptase-normalized supernatants were applied to fresh 293T cells, and infection was allowed to proceed for 96 hr. Infectivity (GFP fluorescence) was then measured by flow cytometry (FACSCalibur, BD Biosciences). For experiments requiring the recovery of retroviral DNA for hypermutation analyses, the viral supernatants were treated with 50 units/ml DNase (Sigma) prior to 293T cell infection.

Figure 15:
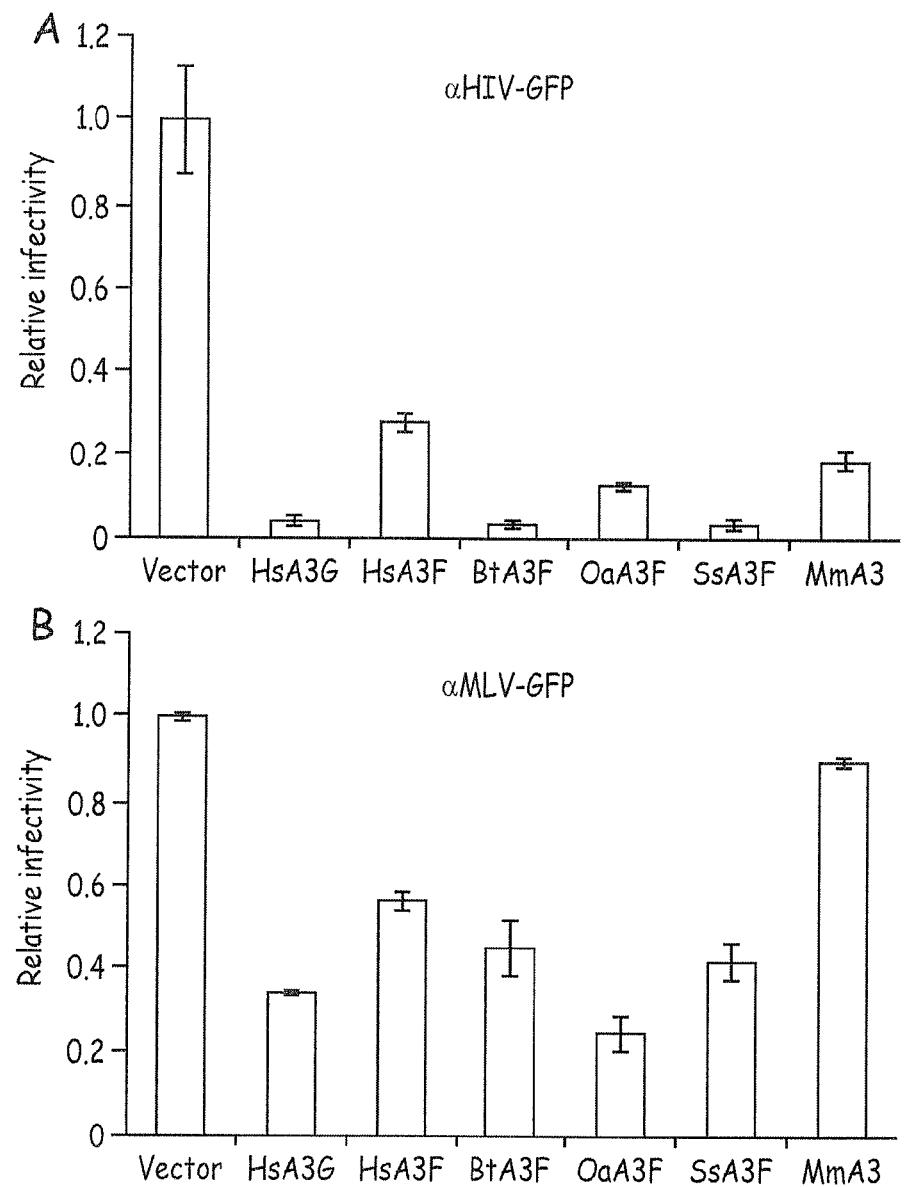
FIG. 15A is a graph of the relative infectivity of HIV-GFP produced in the presence of a vector control or the indicated A3 protein. To facilitate comparisons, all data were normalized to the infectivity of HIV-GFP produced in the presence of a vector control, which was arbitrarily assigned a value of one. The mean and the SEM of three independent experiments are shown. HIV Vif is not present in these experiments.
FIG. 15B is a graph of the relative infectivity of MLV-GFP produced in the presence of the indicated constructs. Parameters are identical to those in FIG. 15A.

Expression of HsA3F and HsA3G caused 4- and 24-fold reductions in the infectivity of HIV-GFP. MmA3 also was capable of strongly inhibiting HIV-GFP. In comparison, expression of BtA3F, OaA3F or SsA3F caused 30-, 8- and 29-fold decreases in the infectivity of HIV-GFP, respectively (FIG. 15A). These potent anti-HIV activities demonstrated that the artiodactyl A3F proteins have at least one retrovirus restriction activity. These results further imply that the artiodactyl A3F proteins are able to specifically associate with the HIV Gag/genomic RNA complex and thereby gain access to assembling virus particles.

HIV-GFP infectivity also was monitored in the presence or absence of HIV-1 Vif and human, artiodactyl or mouse A3 proteins. Expression of HIV-1 Vif neutralized HsA3G and HsA3F (although the latter to a lesser extent) and caused a proportional recovery of HIV-GFP infectivity. Expression of HIV-1 Vif did little to enhance the infectivity of HIV-GFP produced in the presence of MmA3 or any of the artiodactyl A3F proteins. Thus, the artiodactyl A3F proteins were fully resistant to HIV-1 Vif.

Expression of MmA3 has little effect on the infectivity of MLV, presumably because MLV excludes (or simply avoids) this A3 protein (FIG. 15B). In contrast, HsA3F and HsA3G inhibit the infectivity of MLV-based retroviruses, but to a lesser extent than HIV-based viruses (FIG. 15B). Therefore, to begin to ask whether the artiodactyl A3F proteins possess broad, HsA3F- or HsA3G-like, or narrow, MmA3-like retrovirus restriction potentials, the infectivity of MLV-GFP produced in the presence of these A3 proteins was monitored. Interestingly, much like the HsA3F and HsA3G proteins, expression of the artiodactyl A3F proteins reduced the infectivity of MLV-GFP by 2- to 4-fold (FIG. 15B). Thus, the HIV-GFP and MLV-GFP infectivity data combined to suggest that the artiodactyl A3F proteins have a relatively broad retrovirus restriction potential.

Example 11

The N-Terminal Zinc-Binding, Deaminase Domain of the Artiodactyl A3F Proteins Catalyzes C→U Deamination To work-out the mechanism of retrovirus restriction by artiodactyl A3F proteins and to test whether the N- or the C-terminal (or both) zinc-binding domain of these proteins catalyzes DNA cytosine deamination, the conserved glutamate (E) of each active site was changed to glutamine (Q) using site-directed mutagenesis and the resulting mutants were tested for HIV-GFP restriction activity.

As reported previously, the glutamate of both the N- and the C-terminal zinc-binding domain of HsA3G contributes to inhibiting HIV infectivity, but the C-terminal catalytic glutamate appears more important. Both the N- and the C-terminal BtA3F zinc-binding domain E→Q mutants appeared to retain full levels of anti-HIV activity. In contrast, the N-terminal OaA3F and SsA3F zinc-binding domain E→Q mutants were less able than the corresponding C-terminal domain mutants to inhibit the infectivity of HIV-GFP. This result was particularly clear for SsA3F. These data were essentially the inverse of the HsA3F and HsA3G E→Q mutant studies, and they therefore suggested that the N-terminal, zinc-binding domain of these proteins catalyzes retroviral cDNA C→U deamination. MmA3 was clearly distinct, as both the N- and the C-terminal zinc-binding domain glutamates were required for HIV-GFP restriction.

Although both the N- and the C-terminal domain E→Q mutants of the human and the artiodactyl A3 proteins still showed significant levels of anti-retroviral activity, it was surmised that bonafide catalytic site mutants should be unable to catalyze retroviral cDNA C→U deamination [although they may still inhibit retroviral infectivity]. Minus strand uracils template the incorporation of plus strand adenines, ultimately manifesting as retroviral plus strand G→A hypermutations. Therefore, to directly test which zinc-binding domain(s) catalyzes DNA cytosine deamination and to gain additional insight into the artiodactyl A3F retrovirus restriction mechanism, the GFP gene from the aforementioned HIV-GFP infectivity experiments was amplified by high-fidelity PCR, cloned and subjected to DNA sequence analyses. HIV-GFP produced in the presence of a control vector showed a low base substitution mutation frequency, 0.00014 mutations per base, which is attributable to errors in reverse transcription and PCR. In contrast, viruses produced in the presence of HsA3F, HsA3G, all three of the artiodactyl A3F proteins or MmA3 showed between 30- and 80-fold more base substitution mutations, which were almost exclusively retroviral G→A transition mutations. HsA3G with a C-terminal domain E→Q mutation failed to cause retroviral hypermutation, although this variant still significantly inhibited HIV-GFP infectivity. The HsA3F C-terminal zinc-binding domain mutant was still able to modestly inhibit HIV-GFP infectivity, without obvious signs of retroviral hypermutation.

E→Q substitutions in the N-terminal (but not the C-terminal) domain of all three of the artiodactyl A3F proteins abolished the accumulation of retroviral hypermutations. Thus, these data combined to demonstrate that the N-terminal, zinc-binding deaminase domain of the artiodactyl A3F proteins is catalytic and that both deaminase-dependent and -independent activities are required for full levels of retrovirus restriction.

Example 12

Retroviral Hypermutation Properties of Artiodactyl A3F Proteins

As described above, the rpoB mutation spectra of BtA3F, OaA3F and SsA3F suggested that these proteins would trigger retroviral hypermutation patterns biased toward 5'-YC, 5'-GC, and 5'-R C, respectively (R=A or G). To test this prediction, the types of base substitution mutations and the local retroviral cDNA deamination preferences attributable to expression of the artiodactyl A3F proteins was examined. In terms of the dinucleotide mutation preferences, the base immediately 5' of the targeted cytosine is a crucial target site determinant. HsA3F and HsA3G overwhelmingly preferred 5'-CC (84%) and 5'-TC (84%), respectively, whereas MmA3 preferred 5'-TC (61%) and 5'-CC (29%). Like mouse A3, the cow and the sheep A3F proteins appeared to prefer a pyrimidine (Y) 5' of the deaminated cytosine (93% and 79%, respectively). However, roughly paralleling the *E. coli* rpoB mutation data, the pig A3F protein preferred 5'-GC (47%). This is notable because this constitutes the only example of an A3 protein preferring 5'-purine-C (the immunoglobulin gene deaminase AID also has this preference). In addition, all of the A3 proteins characterized in these analyses preferred a pyrimidine at the −2 position (which was invariably a T, except for HsA3G which preferred C>T).

Example 13

Engineered Pigs Expressing APOBEC3F and/or APOBEC3G

Skin fibroblasts from a 9-year old prize boar were transfected with expression constructs encoding human APOBEC3F, human APOBEC3G, or both, and placed under G418 selection. Resistant colonies were picked and expanded. Colonies expressing the APOBEC3F, APOBEC3G, or both were identified by RT-PCR.

Enucleation and Donor Cell Transfer.

In vivo matured ova were surgically recovered from donor animals between 46 and 50 hrs after HCG administration. Immediately prior to enucleation, expanded cumulus and corona cells were removed from both types of ova by blunt dissection and repeated pipetting of the ova in HEPES buffered North Carolina State University 23 (NCSU-23, Petters and Wells (1993) *J Reprod Fertil Suppl.* 48:61-73) medium supplemented with 0.1% hyaluronidase. Groups of ova were transferred into 5 T1 droplets of HEPES buffered NCSU-23 containing 10% fetal calf serum, 2.5 µg/ml cytochalasin B (CB) and 5 Tg/ml Hoechst 33343, which were arranged in a column on the lid of a 9 mm×50 mm Petri dish. Enucleation was achieved by physically removing the polar body and adjacent cytoplasm, containing the metaphase II plate, using an ES cell transfer pipette. Whole cell transfer was accomplished using an ES cell transfer pipette (Eppendorf, Westbury, N.Y.) with a sharp, beveled tip (inner diameter 10-25 μm depending on cell type).

Donor cells (i.e., transfected skin fibroblasts) were synchronized in presumptive G0/G1 by serum starvation (0.5%) for 24 h. Microdrops containing oocytes were spiked with a small volume of donor cells that had been trypsinized not more than 3 h prior to enucleation.

Fusion and Activation of Oocytes.

Donor cells were injected into the perivitelline space and pressed against the oocyte's membrane. Cell-cytoplast couplets were fused within 2 h after enucleation. Groups of 5-10 couplets were manually aligned between the electrodes of a 1 mm gap fusion chamber (BTX, San Diego, Calif., USA) overlaid with mannitol fusion medium (0.28 M mannitol, 0.2 mM $MgSO_4 \times 7H_2O$, 0.01% PVA). Couplets were fused by exposure to a single pulse of 150 V/mm for 60 us. Following fusion, couplets were cultured in HEPES buffered NCSU+10% fetal calf serum from 0.5 to 1.5 h before activation. Couplets were activated by placing them in 1 mm gap fusion chamber overlaid with mannitol medium supplemented with 0.1 mM $CaCl_2 \times 2H_2O$ and exposing them to two 60 microsecond pulses of 150V/mm.

In Vitro Culture of Cloned Embryos.

After activation treatments, the reconstructed cloned embryos were thoroughly washed and cultured in 50 μl drops of NCSU23 supplemented with 1% MEM non essential amino acid, 2% BME amino acids and 0.4 mg/ml BSA for 5 days at 38.5° C. in 5% $CO_2$ in air without a medium change. Following 120 h in culture, fetal calf serum (10%) was added to all microdrops containing reconstructed embryos. The rates of development were examined daily for in vitro cleavage after activation and cleaved embryos at 2-4 cell stages were selected for transfer.

Superovulation and Embryo Transfer.

Pubertal crossbred gilts aged 8 to 10 months were synchronized with Regumate (containing 0.4% altrenogest; 10 mg/day; Intervet, Boxmeer, Netherlands) mixed in commercial feed and given each morning for 17-19 days. All donor gilts were injected with 2,000 IU PMSG (Folligon & Chorulon) and 80 h later with 1,000 IU hCG (Folligon & Chorulon). Recipient gilts were injected with half the dosage of PMSG and hCG administered to the donors. Oocytes were surgically collected 46-50 h after hCG injection by flushing from the oviduct with HEPES buffered NCSU-23.

To produce cloned pigs, reconstructed embryos were surgically transferred into the oviduct of each synchronized foster mother by 20-24 h after activation. Nuclear transfer embryos (N=385) were transferred to three recipients, 2302, 5570 and 2175 on day 1. One week later, an additional group of reconstructed embryos (N=360) was transferred to three additional recipients, 2306, 5638 and 2211. An ultrasound scanner (Aloka SSD-500, JAPAN) with an attached 3.5 MHz transabdominal probe was used to check pregnancies at 25 and 35 days after embryo transfer; five of 6 recipients possessed at least 1 fetus at this time (83%). Five pregnant pigs were obtained. Pregnant recipients were reexamined by ultrasound again at approximately 30 days prior to the expected date of parturition. Recipient 2211 was not pregnant and exhibited estrus approximately 1 month after transplantation, giving an overall 67% pregnancy rate.

One week prior to the date of projected farrowing, all gilts were moved to farrowing crates. Gilts 2302, 5570 and 2175 were given 2 mL of $PGF_{2f}$ on day 113, 112 and 111 of gestation and 2 mL of oxytocin 24 hrs later. On day 118 after embryo transfer, one 700 g male clone was manually removed from recipient 5570. On the same day, recipient 2175 passed one degenerated mummy. The remaining recipient, 2302, who had exhibited substantial milk let-down following her shot of oxytocin, was removed from the crate and given an injection of 15 mL of Lidocaine in a vertebral disk between one set of lower lumbar vertebrae. After waiting 20 minutes for the anesthesia to take effect, a high flank incision was made and both horns of the uterus were exposed. Neither horn contained any fetuses or mummies. However, the endometrium in both horns exhibited extensive cystic hyperplasia, which gave the uterus the appearance of being gravid. Recipient 2302 then was given a general anesthesia (acepromazine+ketamine) and euthanized. Recipient 2175 was also anesthetized and euthanized and her uterus examined for the presence additional mummies or fetuses; none were found.

On day 112 of gestation, recipient 5638 received 2 mL of $PGF_{2f}$. Oxytocin (2 mL) was administered at 6 AM the following day. At 7:20 AM, the first of five male clones was manually removed from the recipient. By 11:00 AM, a total of 5 male clones had been delivered. Thus, 6 live-born transgenic clones were generated from a total of 6 recipients.

All clones exhibited from moderate to severe arthrogryposis in the rear legs, which greatly reduced their mobility. Clone 1 (700 g) was manually removed from recipient 5570 but was unable to nurse so was photographed and euthanized the next day. Clones 2 (1000 g) and 3 (700 g) died within a few hours of birth. Clone 4 (700 g), who had a fairly severe case of arthrogryposis, died later on the same day. Clones 5 (1200 g) and 6 (1200 g) were manually fed hourly, via syringe and mouse feeding needle, with Esbilac (milk replacement formula). Clone 6's health visibly improved during this nursing period, while clone 5's health declined. Clone 5 was extremely weak and no longer swallowing Esbilac and was euthanized the next day. Clone 6 was returned to his dam and was viable for 2 weeks, but had major abscesses on the tops of his rear feet and his swollen front pasterns. Daily injections of Tylan 200 and penicillin did not resolve this condition so the piglet was euthanized and cells were harvested.

Epigenetic reprogramming may be deficient in cloned embryos. Nuclei can be more effectively reprogrammed by passing them through multiple rounds of cloning and fetal fibroblast isolation before carrying piglets to term. Transgenic cells already produced can be used to generate reconstructed embryos, which would then be implanted and left to develop for about 40 days before the termination of pregnancy. Fibroblasts would then be isolated from these fetuses and cultured briefly before use in another round of somatic cell nuclear transfer to generate new piglets. Another alternative would rely on the use of fetal fibroblasts to start with, i.e., using fetal fibroblasts to generate new transgenic cells expressing the APOBEC proteins, and then generating pigs by somatic cell nuclear transfer as described above. Most successful pig cloning experiments have utilized cells derived from fetal fibroblasts, as opposed to the aged boar used in this example. Other sources of cells, including embryonic or adult stem cells also can be used.

Other Embodiments

While the invention has been described in conjunction with the foregoing detailed description and examples, the foregoing description and examples are intended to illustrate and not to limit the scope of the invention, which is defined by the scope of the appended claims. Other aspects, advantages, and modifications are within the scope of the claims.

What is claimed is:

1. A transgenic pig, the nucleated cells of which comprise a nucleic acid construct, said nucleic acid construct comprising a transcriptional unit comprising a regulatory region operably linked to a nucleic acid sequence encoding a non-porcine APOBEC3 cytosine deaminase polypeptide.

2. The transgenic pig of claim 1, wherein said regulatory region is a constitutive promoter.

3. The transgenic pig of claim 1, wherein said porcine regulatory region is a tissue-specific or an organ-specific promoter.

4. The transgenic pig of claim 1, wherein an insulator element and an inverted repeat of a transposon flank each side of said transcriptional unit.

5. The transgenic pig of claim 1, wherein said non-porcine APOBEC3 cytosine deaminase is selected from the group consisting of APOBEC3A, APOBEC3B, APOBEC3C, APOBEC3D, APOBEC3E, APOBEC3F, APOBEC3G, and APOBEC3H.

6. The transgenic pig of claim 1, wherein said non-porcine APOBEC3 cytosine deaminase is human ABOBEC3G.

7. Transgenic cells derived from the transgenic pig of claim 1.

8. Transgenic tissue isolated from the transgenic pig of claim 1.

9. Transgenic progeny of said transgenic pig of claim 1.

10. The transgenic pig of claim 1, wherein said non-porcine APOBEC3 cytosine deaminase is human APOBEC3F.

11. The transgenic pig of claim 1, wherein expression of said non-porcine APOBEC3 cytosine deaminase polypeptide in at least some of the cells of the pig results, upon co-culture with human cells, in decreased capability of said cells to transmit porcine endogenous retroviruses to the human cells.

* * * * *